US012780829B2

(12) United States Patent
MacKeigan et al.

(10) Patent No.: US 12,780,829 B2
(45) Date of Patent: Nov. 3, 2026

(54) ULK1 AND ULK2 INHIBITORS

(71) Applicant: Board of Trustees of Michigan State University, East Lansing, MI (US)

(72) Inventors: Jeffrey P. MacKeigan, Grand Rapids, MI (US); Edmund Ellsworth, Vicksburg, MI (US); Katie R. Martin, Rockford, MI (US); Bilal Abou Aleiwi, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 282 days.

(21) Appl. No.: 18/719,712

(22) PCT Filed: Dec. 22, 2022

(86) PCT No.: PCT/US2022/082283
§ 371 (c)(1),
(2) Date: Jun. 13, 2024

(87) PCT Pub. No.: WO2023/122756
PCT Pub. Date: Jun. 29, 2023

(65) Prior Publication Data

US 2025/0059194 A1 Feb. 20, 2025

Related U.S. Application Data

(60) Provisional application No. 63/292,877, filed on Dec. 22, 2021.

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC ............................ C07D 487/04; A61K 31/519
See application file for complete search history.

(56) References Cited

U.S. PATENT DOCUMENTS

| | | | |
|---|---|---|---|
| 7,585,875 | B2 | 9/2009 | Gaeta et al. |
| 8,461,162 | B2 | 6/2013 | Stanton et al. |
| 2011/0195933 | A1 | 8/2011 | Katz et al. |
| 2013/0210838 | A1 | 8/2013 | Lim et al. |
| 2014/0271667 | A1 | 9/2014 | Altieri et al. |
| 2019/0152989 | A1 | 5/2019 | Shaw et al. |

FOREIGN PATENT DOCUMENTS

| | | | |
|---|---|---|---|
| WO | WO-2011050284 | A1 | 4/2011 |
| WO | WO-2023122756 | A2 | 6/2023 |
| WO | WO-2023122756 | A3 | 9/2023 |

OTHER PUBLICATIONS

"International Application Serial No. PCT US2022 082283, International Preliminary Report on Patentability mailed Jul. 4, 2024", 7 pages.
Martin, Katie R., "A Potent and Selective ULK1 Inhibitor Suppresses Autophagy and Sensitizes Cancer Cells to Nutrient Stress", Iscience 8, (Sep. 19, 2018), 20 pages.
Tang, Fang, "SBI0206965, a novel inhibitor of Ulk1, suppresses non-small cell lung cancer cell growth by modulating both autophagy and apoptosis pathways", Oncology Reports 37, (May 2017), 10 pages.
"International Application Serial No. PCT/US2022/082283, International Search Report mailed Jul. 11, 2023", 4 pgs.
"International Application Serial No. PCT/US2022/082283, Invitation to Pay Additional Fees mailed Mar. 21, 2023", 2 pgs.
"International Application Serial No. PCT/US2022/082283, Written Opinion mailed Jul. 11, 2023", 5 pgs.

*Primary Examiner* — San Ming R Hui
(74) *Attorney, Agent, or Firm* — McKee, Voorhees & Sease, PLC

(57) ABSTRACT

Novel compounds, pharmaceutical compositions comprising same, and methods of treating a cancer and autophagy related diseases.

19 Claims, No Drawings

ULK1 AND ULK2 INHIBITORS

CROSS-REFERENCE TO RELATED APPLICATIONS

This application is a U.S. national stage filing under 35 U.S.C. § 371 from International Application No. PCT/US2022/082283, filed on 22 Dec. 2022, and published as WO 2023/122756 on 29 Jun. 2023, which claims priority to U.S. provisional patent application No. 63/292,877, which was filed on Dec. 22, 2021, the disclosures of which are hereby incorporated by reference in their entirety.

BACKGROUND

Macroautophagy (hereafter, autophagy) is an intracellular recycling pathway that generates biochemical building blocks through cytoplasmic breakdown (Klionsky, 2007). This process begins with nucleation of cup-shaped structures (phagophores) that grow into double-membrane autophagosomes as they sequester portions of cytosol. Fusion with lysosomes provides degradative enzymes to catabolize cargo into amino acids, lipids, and carbohydrates, which are then available for the cell to reuse. As an energy-efficient alternative to de novo synthesis, autophagy can promote cell survival during times of stress (Rabinowitz and White, 2010). For this reason, this process can contribute to the progression of certain cancers (e.g., by enabling survival in a nutrient-depleted tumor microenvironment) and also to therapeutic resistance. Autophagy appears to be particularly important in the survival and growth of KRAS-driven tumors, as evidenced in part by data from genetic mouse models (Eng et al., 2016; Guo et al., 2013; Guo et al., 2016; Karsli-Uzunbas et al., 2014; Rao et al., 2014). Autophagy inhibition is now being explored as a means to improve efficacy of existing cancer treatments, as well as a therapeutic strategy of its own (Chude and Amaravadi, 2017).

Autophagy induction is controlled primarily by the serine/threonine kinase, ULK1 (unc-51 like autophagy initiating kinase 1), a mammalian ortholog of yeast ATG1. ULK1 is part of a complex with binding partners ATG13 (autophagy related 13), RB1CC1 (RB1 inducible coiled-coil; also known as FIP200), and ATG101 (autophagy related 101) (Ganley et al., 2009; Mercer et al., 2009). Through this complex, ULK1 integrates upstream signals from both the MTOR nutrient-sensing and the AMPK energy-sensing pathways to induce production of early autophagic membranes (Ganley et al., 2009; Hosokawa et al., 2009; Jung et al., 2009; Kim et al., 2011). ULK1's essential role in autophagy has been shown in animals and mammalian cell culture systems where ULK1 depletion impairs autophagy (Chan et al., 2007; Cheong et al., 2011; Lee and Tournier, 2011). Although a second mammalian ATG1 ortholog, ULK2, also promotes autophagy (Lee and Tournier, 2011), loss of ULK1 alone is sufficient to abrogate autophagy in many cell types, underscoring its particularly important role (Chan et al., 2007; Zachari and Ganley, 2017)

ULK1 (unc-51 like autophagy initiating kinase 1), a serine/threonine kinase, has emerged as the gatekeeper to autophagy, controlling the initiation of this process. ULK1 is considered the lead target for autophagy inhibition because of its role in pathway activation, druggable nature, and selectivity for autophagy over other cellular functions. High ULK1 expression associates with poor prognosis and therapeutic resistance in cancer and reduced patient survival.

Regarding conventional chemotherapeutic, ULK1 inhibition induced apoptotic cell death in NSCLC cell lines and sensitized cells to cisplatin treatment. Additionally, a combination of autophagy inhibition and small molecule pathway therapeutics have shown positive results in combination. Moreover, autophagy promotes immune evasions by a few mechanisms, such as degrading MHC-I or inhibiting T-cell immune responses, resulting in immunologically cold tumors becoming immunologically hot tumors. Together, this suggests that ULK1 expression associates with advanced NSCLC, which could involve promoting autophagy-mediated tumor cell survival and immune evasion, strengthening the rationale for its therapeutic targeting in many cancer contexts, such as KRAS NSCLC.

Autophagy plays an essential role in maintaining protein quality control, while defective autophagy is involved in the development of diseases including, but not limited to, cancer, neurodegenerative disorders, autoimmune disorders, cardiovascular disorders, metabolic disorders, hamartoma syndrome, genetic muscle disorders, and myopathies. Therefore, there exists a need for identification of inhibitors of the autophagy survival pathway in, for example, cancer cells. Such inhibitors of autophagy can be used in the prevention, palliation, and/or treatment of cancer.

Autophagy dysfunction is a major contributor to diseases including, but not limited to, neurodegeneration, liver disease, and cancer. Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include capsase dependent and independent pathways, autophagy, necrosis, apoptosis, and mitochondrial dependent and independent processes.

Lung cancer is the most common cancer worldwide. RAS is the most frequent oncogene in cancer with mutations of KRAS, NRAS, and HRAS occurring in 30% of cases. Despite significant advances in precision medicine, lung cancer patients with KRAS mutations still face poor prognosis. Therefore, new therapeutics must be developed to improve prognosis. Successfully targeting autophagy is a critical next step in cancer research, and success in this endeavor will lead to novel treatment options for cancer patients.

SUMMARY

The disclosure relates to a compound of Formula (I) or (II):

(I)

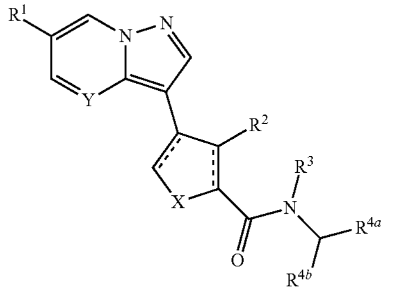

(II)

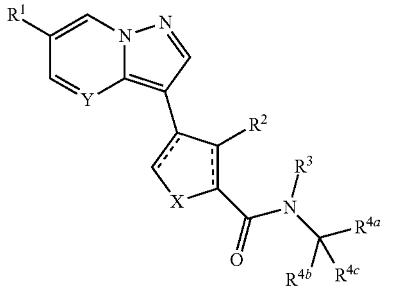

wherein:

$R^1$ is —$N(R^3)_2$, —$N(R^3)$-cycloalkyl, N-attached heterocyclyl, $N(R^3)C(O)OtBu$, —$N(R^3)$-alkylene-aryl, —$N(R^3)$-alkylene-heterocyclyl, —$N(R^3)$aryl, or —$N(R^3)$ heterocyclyl;

$R^2$ is H, halo, —CN, —$NO_2$, alkyl, —O-alkyl, —C(O)-alkyl;

$R^3$ is independently H or $C_{1-4}$ alkyl;

$R^{4a}$ and $R^{4b}$ are independently $C_{1-4}$-alkyl, alkylene-OH, alkylene-$N(R^3)C(O)OtBu$, alkylene —$N(R^3)C(O)$ OtBu alkylene-cycloalkyl, cycloalkyl, $CF_3$, or can be taken together to form a 4-7-membered ring;

$R^{4c}$ is H or methyl;

X is O, $NR_3$, or S;

Y is CH or N; and $\overline{\underline{---}}$ is a single or a double bond;

or a pharmaceutically acceptable salt thereof.

The disclosure further relates to a pharmaceutical composition comprising a therapeutically effective amount of one or more compounds and a pharmaceutically acceptable carrier.

Also disclosed are methods of treating cancer, neurodegenerative disorders, autoimmune disorders, cardiovascular disorders, metabolic disorders, hamartoma syndrome, genetic muscle disorders, and myopathies. The method comprises administering a therapeutically effective amount of one or more compounds of formula I or II, or a pharmaceutical composition comprising same, to a patient in need thereof.

DETAILED DESCRIPTION

While the concepts of the present disclosure are illustrated and described in detail in the figures and descriptions herein, results in the figures and their description are to be considered as examples and not restrictive in character; it being understood that only the illustrative embodiments are shown and described and that all changes and modifications that come within the spirit of the disclosure are desired to be protected.

The disclosure relates to compounds that inhibit ULK1. The compounds are useful for the treatment of cancer.

Compounds

The disclosure relates to a compound of Formula (I) or (II):

(I)

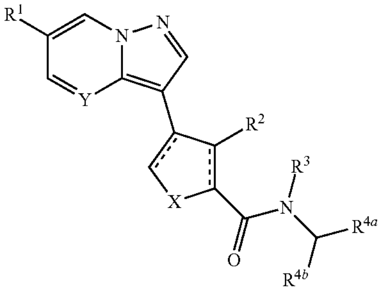

(II)

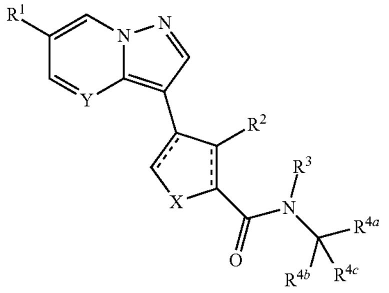

wherein:

$R^1$ is —$N(R^3)_2$, —$N(R^3)$-cycloalkyl, N-attached heterocyclyl, $N(R^3)C(O)OtBu$, —$N(R^3)$-alkylene-aryl, —$N(R^3)$-alkylene-heterocyclyl, —$N(R^3)$ aryl, or —$N(R^3)$ heterocyclyl;

$R^2$ is H, halo, —CN, —$NO_2$, alkyl, —O-alkyl, —C(O)-alkyl;

$R^3$ is independently H or $C_{1-4}$-alkyl;

$R^{4a}$ and $R^{4b}$ are independently $C_{1-4}$ alkyl, alkylene-OH, alkylene-$N(R^3)C(O)OtBu$, alkylene-$N(R^3)C(O)OtBu$ alkylene-cycloalkyl, cycloalkyl, $CF_3$, or can be taken together to form a 4-7-membered ring;

$R^{4c}$ is H or methyl;

X is O, $NR_3$, or S;

Y is CH or N; and $\overline{\underline{---}}$ is a single or a double bond;

or a pharmaceutically acceptable salt thereof.

The disclosure relates to compounds of Formula (Ia), or (Ib):

(Ia)

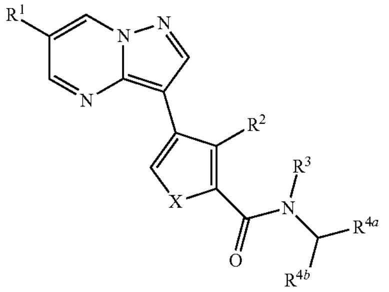

(Ib)

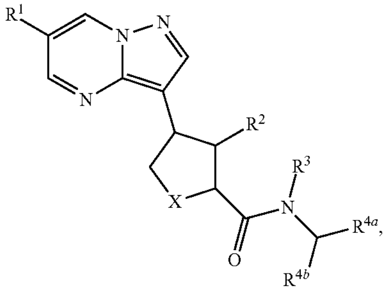

or a pharmaceutically acceptable salt thereof.

The disclosure relates to compounds of Formula (Ic), or (Id):

(Ic)

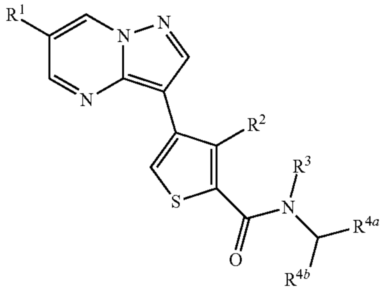

(Id)

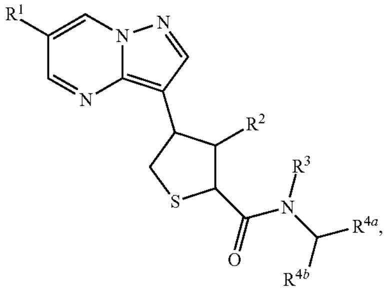

or a pharmaceutically acceptable salt thereof.

The disclosure relates to compounds of Formula (Ie), or (If):

(Ie)

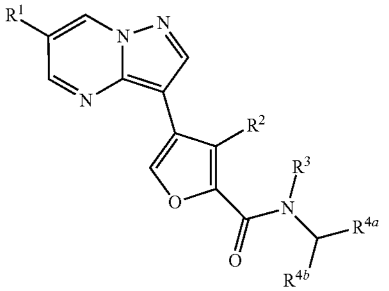

(If)

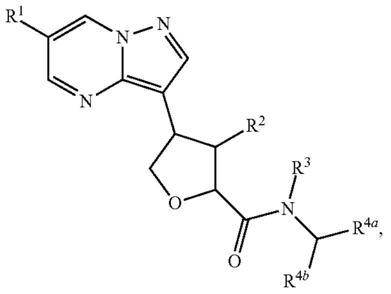

or a pharmaceutically acceptable salt thereof.

The disclosure relates to compounds of Formula (Ig), or (Ih):

(Ig)

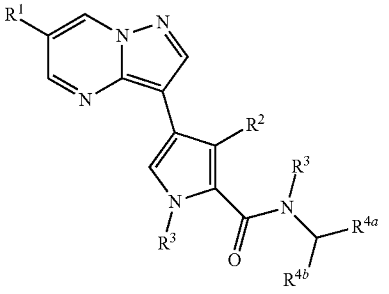

(Ih)

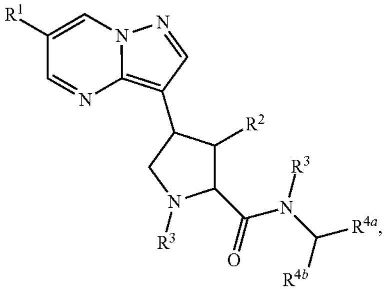

or a pharmaceutically acceptable salt thereof.

The disclosure relates to compounds of Formula (Ii), or (Ij):

(Ii)

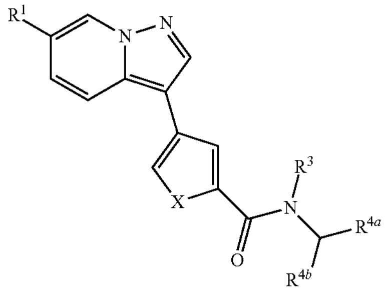

(Ij)

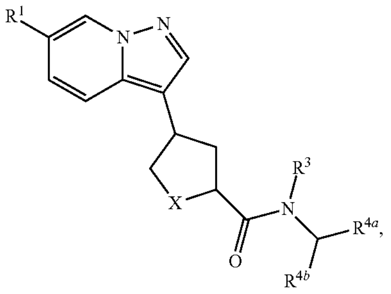

or a pharmaceutically acceptable salt thereof.

The disclosure relates to compounds of Formula (Ik), or (Il):

(Ik)

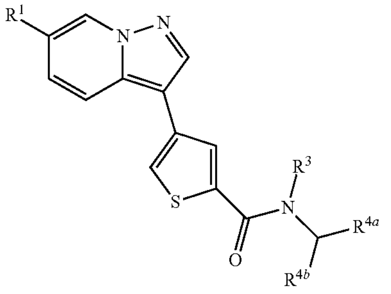

(Il)

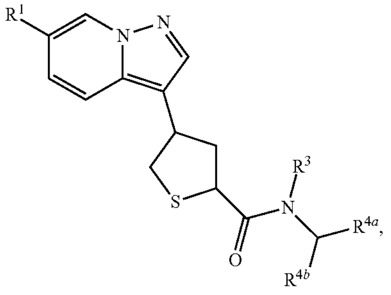

or a pharmaceutically acceptable salt thereof.

The disclosure relates to compounds of Formula (Im), or (In):

(Im)

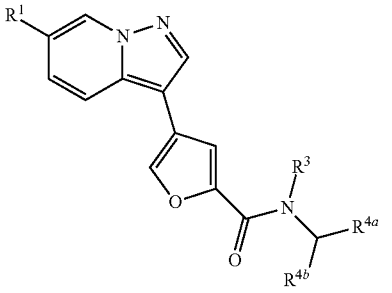

(In)

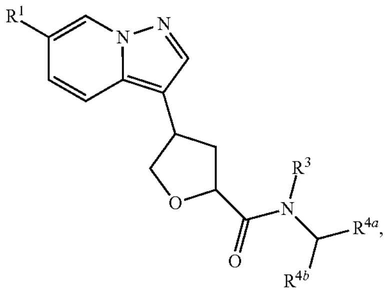

or a pharmaceutically acceptable salt thereof.

The disclosure relates to compounds of Formula (Io), or (Ip):

(Io)

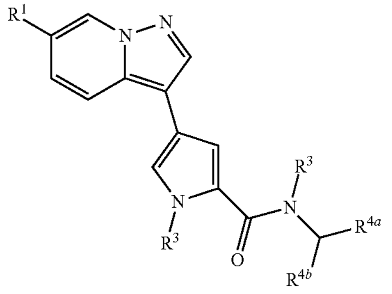

(Ip)

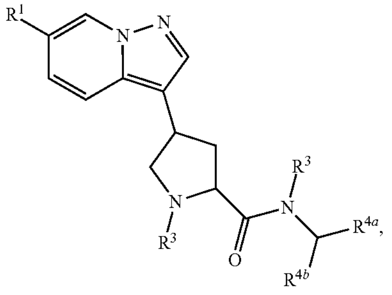

or a pharmaceutically acceptable salt thereof.

The disclosure relates to compounds of Formula (Ia), or (IIb):

(IIa)

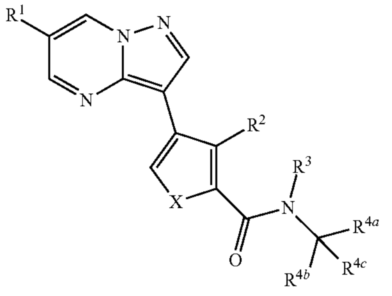

(IIb)

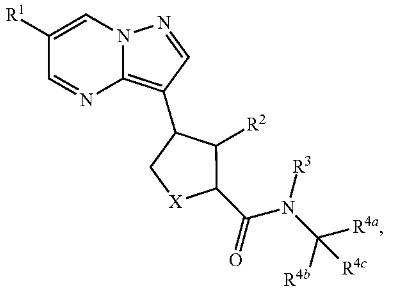

or a pharmaceutically acceptable salt thereof.

The disclosure relates to compounds of Formula (IIc), or (IId):

(IIc)

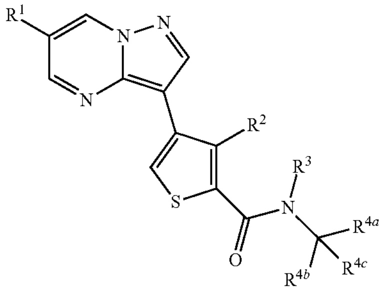

(IId)

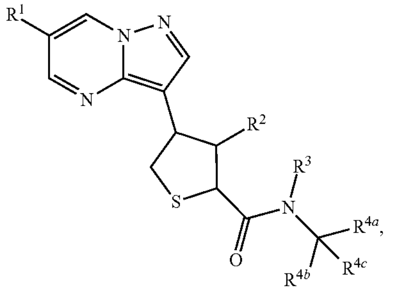

or a pharmaceutically acceptable salt thereof.

The disclosure relates to compounds of Formula (Le), or (IIf):

(IIe)

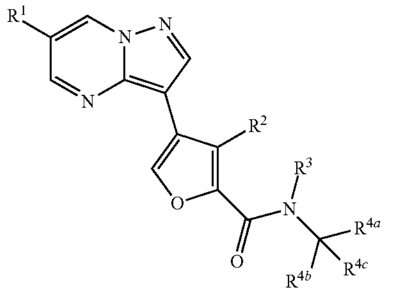

(IIf)

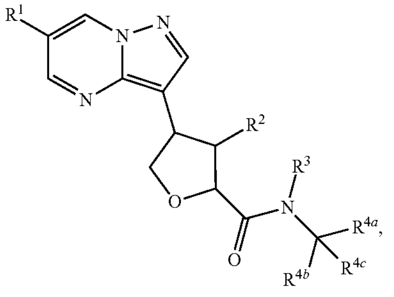

or a pharmaceutically acceptable salt thereof.

The disclosure relates to compounds of Formula (IIg), or (IIh):

(IIg)

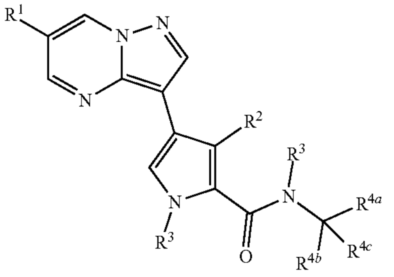

(IIh)

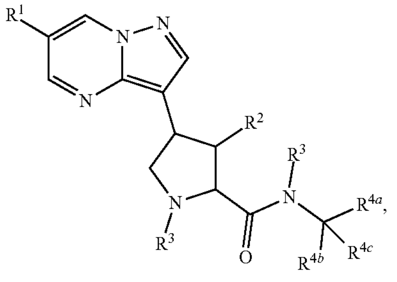

or a pharmaceutically acceptable salt thereof.

The disclosure relates to compounds of Formula (Ii), or (IIj):

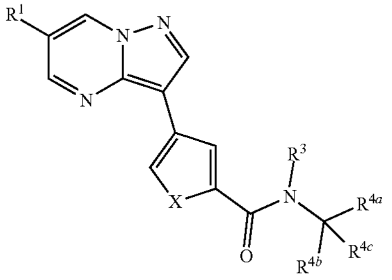
(IIi)

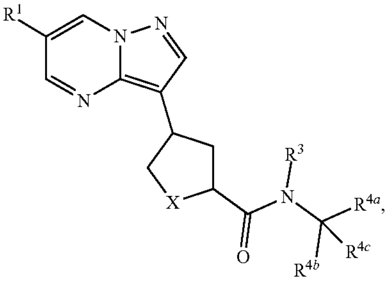
(IIj)

or a pharmaceutically acceptable salt thereof.

The disclosure relates to compounds of Formula (IIk), or (III):

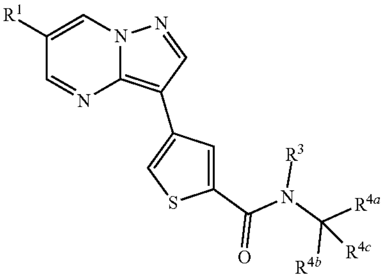
(IIk)

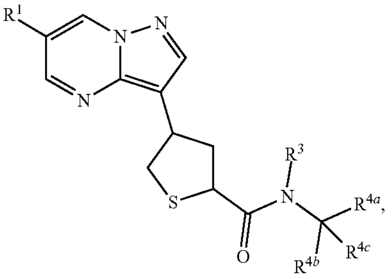
(III)

or a pharmaceutically acceptable salt thereof.

The disclosure relates to compounds of Formula (Im), or (IIn):

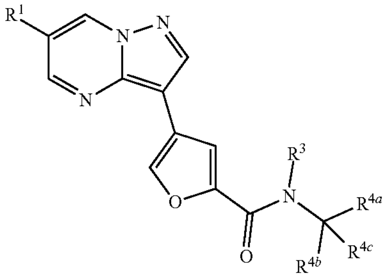
(IIm)

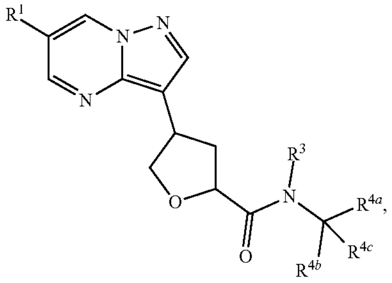
(IIn)

or a pharmaceutically acceptable salt thereof.

The disclosure relates to compounds of Formula (IIo), or (IIp):

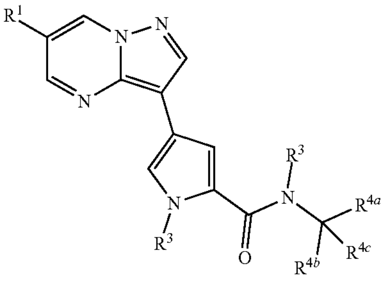
(IIo)

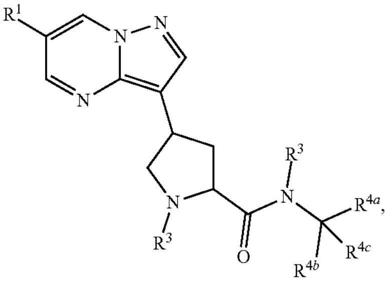
(IIp)

or a pharmaceutically acceptable salt thereof.

Throughout the disclosure:

X can be O. X can be $NR_3$. X can be S.

In combination with the foregoing X groups:

Y can be CH. Y can be N.

In combination with the foregoing X and Y groups:

$R^1$ can be —$N(R^3)_2$—. $R^1$ can be —$N(R^3)$-cycloalkyl. $R^1$ can be N-attached heterocyclyl. $R^1$ can be —$N(R^3)$ aryl. $R^1$ can be $N(R^3)$—$C_{5-8}$-aryl. $R^1$ can be —$N(R^3)$ heterocyclyl. $R^1$ can be $N(R^3)$—$C_{5-8}$-heterocyclyl. $R^1$ can be $N(R^3)C(O)OtBu$. $R^1$ can be N(H)C(O)OtBu. $R^1$ can be —$N(R^3)$-alkylene-aryl. $R^1$ can be —$N(R^3)$-alkylene-heterocyclyl. $R^1$ can be N(H)aryl. $R^1$ can be N(H)heterocyclyl. $R^1$ can be substituted or unsubstituted.
$R^1$ can be
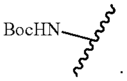
$R^1$ can be
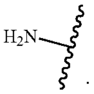
$R^1$ can be
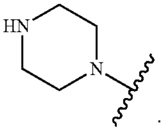
$R^1$ can be
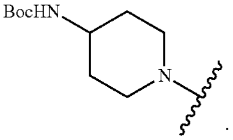 [SMILES: *N1CCC(NC(=O)OC(C)(C)C)CC1]
$R^1$ can be
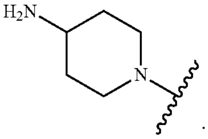 [SMILES: *N1CCC(N)CC1]
$R^1$ can be
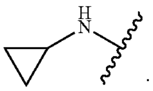
$R^1$ can be
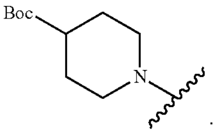 [SMILES: *N1CCC(C(=O)OC(C)(C)C)CC1]
$R^1$ can be
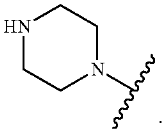
$R^1$ can be
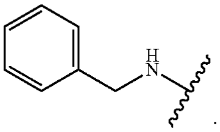 [SMILES: *NCc1ccccc1]
$R^1$ can be
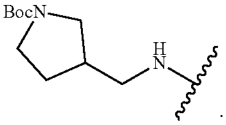 [SMILES: *NCC1CCN(C(=O)OC(C)(C)C)C1]
$R^1$ can be
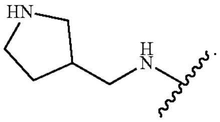 [SMILES: *NCC1CCNC1]
$R^1$ can be
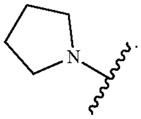 [SMILES: *N1CCCC1]
$R^1$ can be
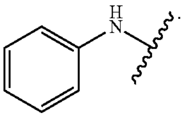 [SMILES: *Nc1ccccc1]
$R^1$ can be
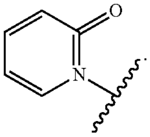

$R^1$ can be

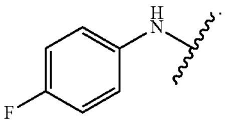 [SMILES: *Nc1ccc(F)cc1]

$R^1$ can be

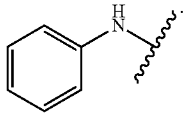 [SMILES: *Nc1ccccc1]

$R^1$ can be

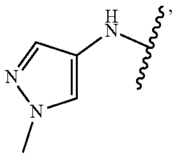 [SMILES: *Nc1cnn(C)c1]

In combination with the foregoing X, Y, and $R^1$ groups:

$R^2$ can be H. $R^2$ can be halo. $R^2$ can be —CN. $R^2$ can be —$NO_2$. $R^2$ can be alkyl. $R^2$ can be —O-alkyl. $R^2$ can be —C(O)-alkyl.

In combination with the foregoing X, Y, $R^1$ and $R^2$ groups:

$R^3$ can be H. $R^3$ can be $C_{1-4}$ alkyl. $R^3$ can be methyl.

In combination with the foregoing X, Y, $R^1$, $R^2$ and $R^3$ groups:

$R^{4a}$ can be $C_{1-4}$-alkyl. $R^{4a}$ can be methyl. $R^{4a}$ can be ethyl. $R^{4a}$ can be alkylene —OH. $R^{4a}$ can be alkylene —N($R^3$)C(O)OtBu. $R^{4a}$ can be alkylene —N(H)C(O)OtBu $R^{4a}$ can be alkylene-cycloalkyl. $R^{4a}$ can be $CF_3$ $R^{4a}$ can be —C(Me)$CH_2$OH. $R^{4a}$ can be —C(H)$CH_2CH_3$. $R^{4a}$ can be —$(CH_2)_2$N(H)Boc. $R^{4a}$ can be alkylene-cycloalkyl. $R^{4a}$ can be cycloalkyl. $R^{4a}$ can be cyclopropyl. $R^{4a}$ can be $CF_3$. $R^{4a}$ can be —$CH_2$—OH.

$R^{4b}$ can be $C_{1-4}$ alkyl. $R^{4b}$ can be methyl. $R^{4a}$ can be ethyl. $R^{4b}$ can be alkylene-OH. $R^{4b}$ can be alkylene-N($R^3$)C(O)OtBu. $R^{4b}$ can be alkylene-N(H)C(O)OtBu $R^{4b}$ can be alkylene-cycloalkyl. $R^{4b}$ can be $CF_3$ $R^{4b}$ can be —C(Me)$CH_2$OH. $R^{4b}$ can be —C(H)$CH_2CH_3$. $R^{4b}$ can be —$(CH_2)_2$N(H) Boc. $R^{4b}$ can be alkylene-cycloalkyl. $R^{4b}$ can be cycloalkyl. $R^{4b}$ can be cyclopropyl. $R^{4b}$ can be $CF_3$. $R^{4b}$ can be —$CH_2$—OH.

$R^{4b}$ can be $C_{1-4}$alkyl. $R^{4b}$ can be alkylene —OH. $R^{4b}$ can be alkylene-N(H)C(O)OtBu.

$R^{4c}$ can be H. $R^{4c}$ can be methyl.

$R^{4a}$ and $R^{4b}$ can be taken together to form a 4-7-membered ring. The 4-7-membered ring can be substituted or unsubstituted. The 4-7-membered ring can be

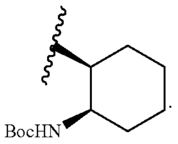

The 4-7-membered ring can be

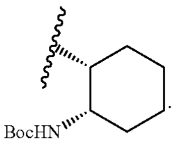 [SMILES: *[C@@H]1CCCC[C@@H]1NC(=O)OC(C)(C)C]

The 4-7-membered ring can be

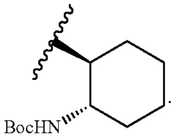 [SMILES: *[C@H]1CCCC[C@@H]1NC(=O)OC(C)(C)C]

The 4-7-membered ring can be

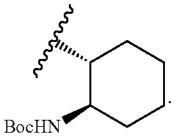

The 4-7-membered ring can be

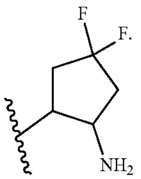

The 4-7-membered ring can be

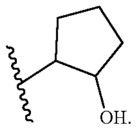

The 4-7-membered ring can be

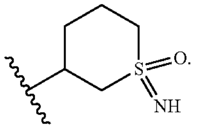 [SMILES: *C1CCCS(=N)(=O)C1]

In combination with the foregoing X, Y, $R^1$, $R^2$, $R^3$, $R^{4a}$, $R^{4b}$ and $R^{4c}$ groups:

⎓ can be a single.

⎓ can be a double bond.

Alkyl, alkylene, aryl, cycloalkyl, heterocyclyl, and bicyclyl can be substituted with one or more groups selected from alkyl, aryl, heterocyclyl, halo, hydroxy, alkoxy, amino, nitro, sulfhydryl, imino, amido, sulfamoyl, sulfinyl, alkylthio, sulfonyl, ketone, a heterocyclyl, —CN, —$NO_2$, —$C(O)_2$-alkyl, —$C(O)_2$-alkyl, —$C(O)NH_2$, —N(H)CO-alkyl, —N(H)-alkylene-aryl, —$C(F_2)CH_3$, —$CF_3$, —$C(F)H_2$, S-alkyl $SO_2$-halo, or O-aryl. If a moiety is substituted with two or more substituents, the substituents can be the same or different. Two substituents can be taken together to form a ring.
The compound formula (I) or (II) can be selected from:
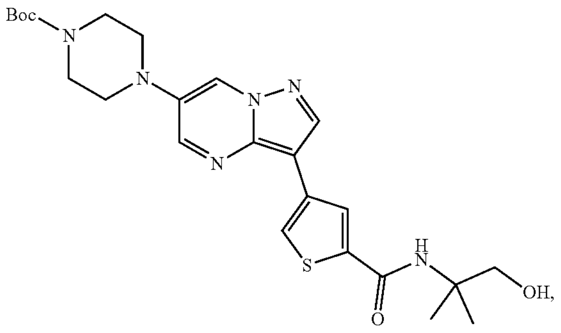
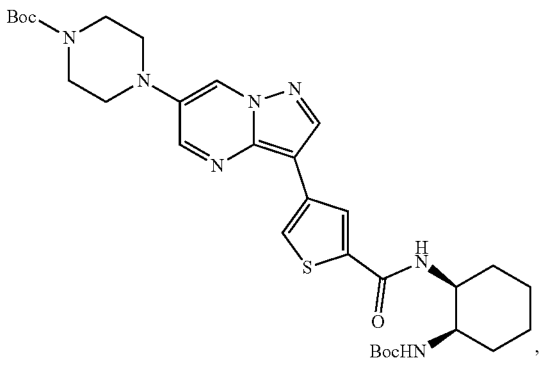
,
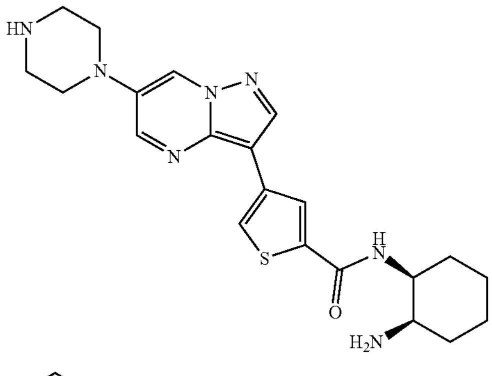
,
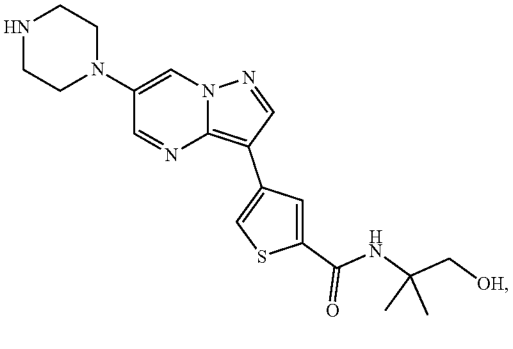
-continued
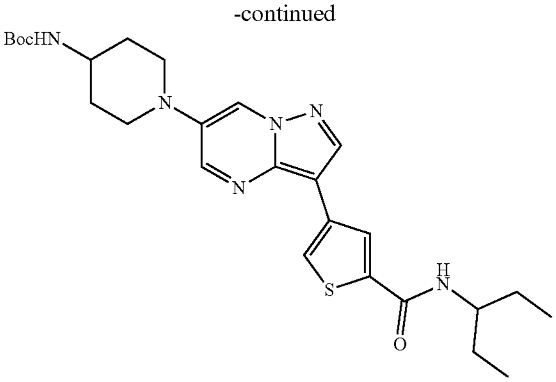
,
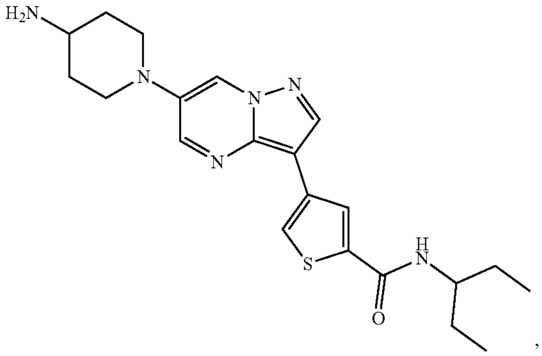
,
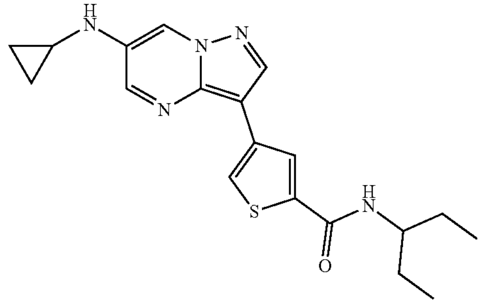
,
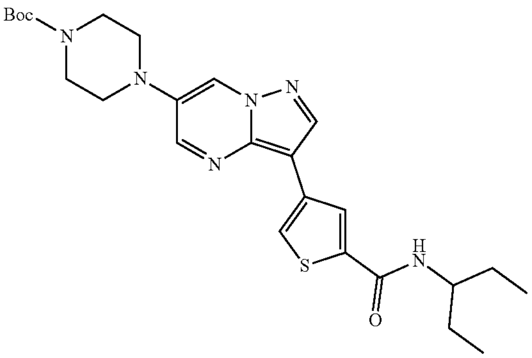
,
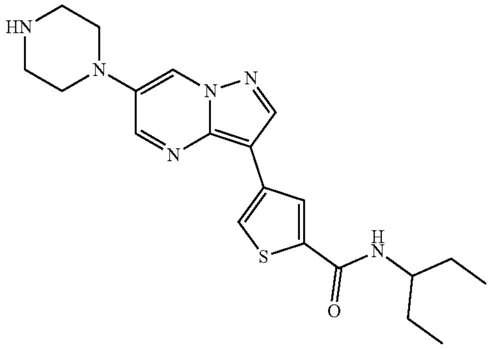
, -continued
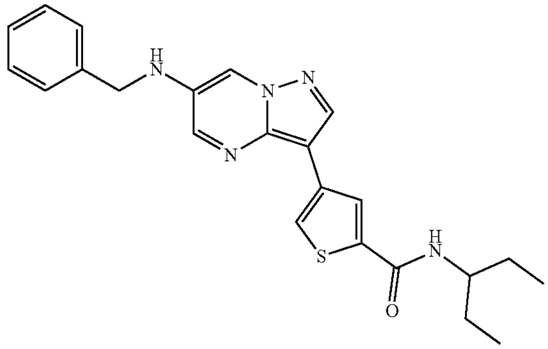
,
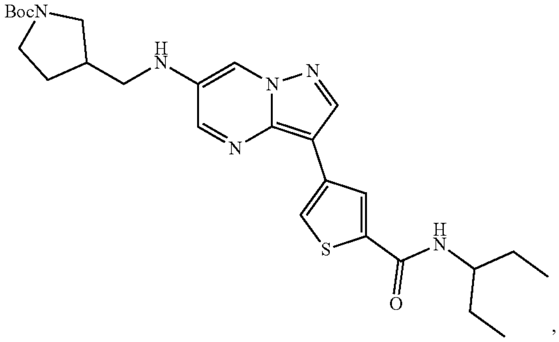
,
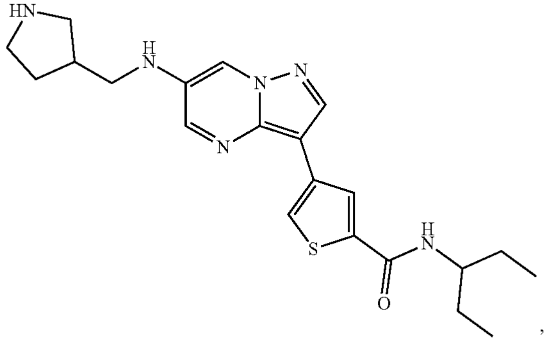
,
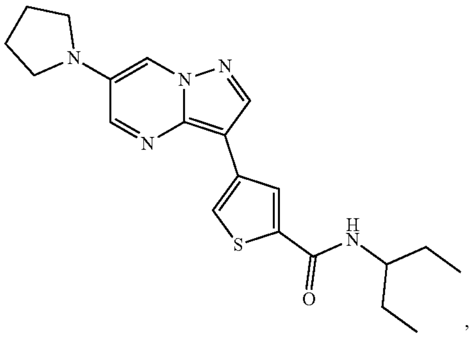
,
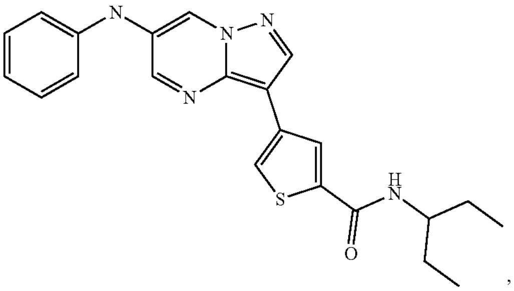
, and
-continued
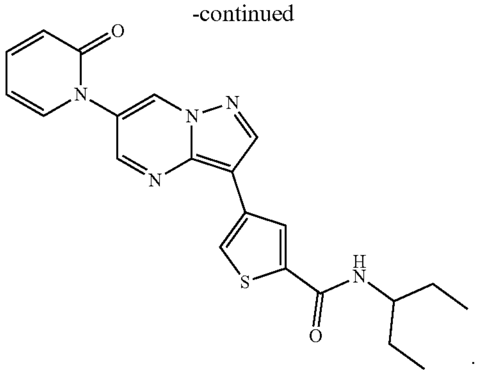
.
The compound formula (I) or (II) can be selected from:
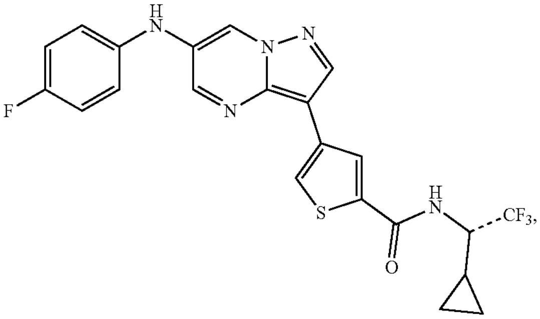
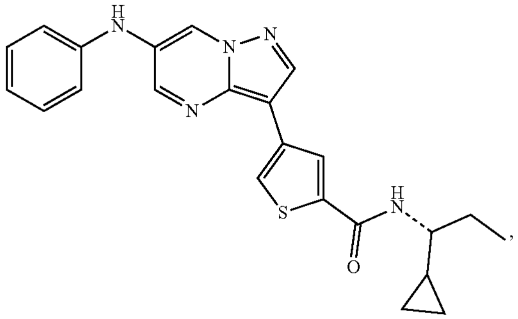
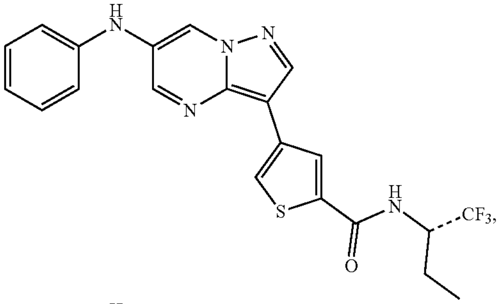
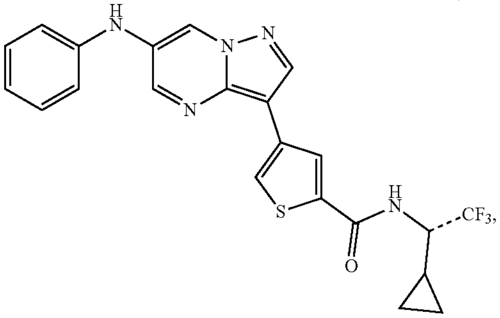

-continued

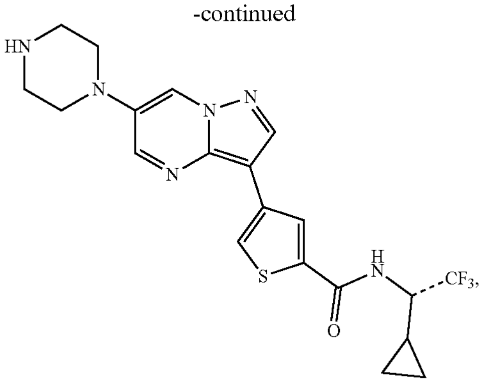

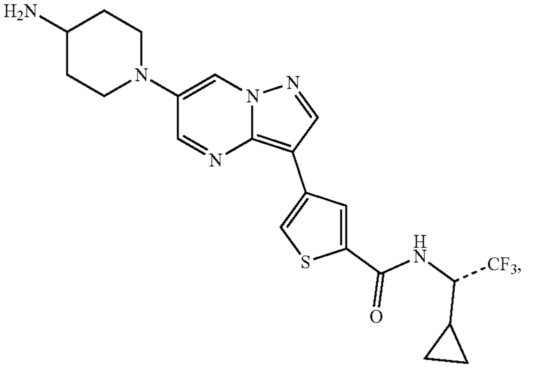

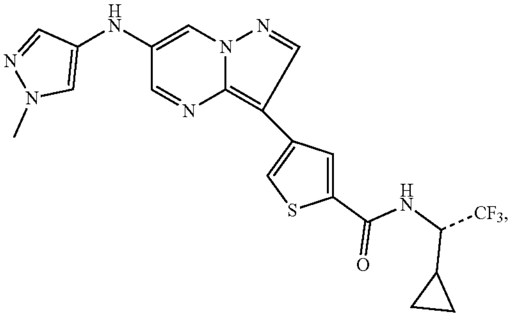

and

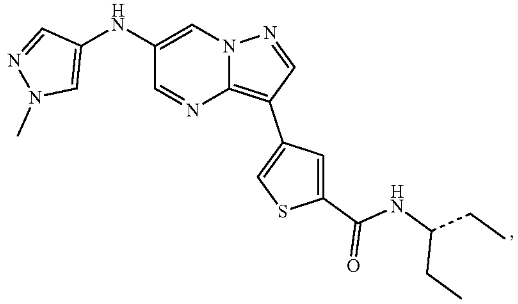

The compound formula (I) or (II) can be selected from Table 1.

All diastereomers of the compounds of the formula (I) are contemplated herein.

Also contemplated herein are isotopomers, which are compounds where one or more atoms in the compound has been replaced with an isotope of that atom. Thus, for example, the disclosure relates to compounds wherein one or more hydrogen atoms is replaced with a deuterium or wherein a fluorine atom is replaced with an 19F atom.

Methods of Treatment

The disclosure relates to a method of treating a cancer comprising the step of administering to a subject in need thereof a therapeutically effective amount of any one of the aforementioned compounds or a pharmaceutical composition comprising same. The cancer can be a cancer with KRAS mutation.

Accordingly, the disclosure provides methods to treat a cancer, comprising administering to a subject suffering therefrom a therapeutically effective amount of a ULK1 inhibitor or a pharmaceutical composition comprising same.

The disclosure relates to a method of treating an autophagy related disease comprising the step of administering to a subject in need thereof a therapeutically effective amount of any one of the aforementioned compounds or a pharmaceutical composition comprising same. Autophagy plays an essential role in maintaining protein quality control, while defective autophagy is involved in the development of diseases including, but not limited to, cancer, neurodegenerative disorders, autoimmune disorders, cardiovascular disorders, metabolic disorders, hamartoma syndrome, genetic muscle disorders, and myopathies. Therefore, there exists a need for identification of inhibitors of the autophagy survival pathway in, for example, cancer cells. Such inhibitors of autophagy can be used in the prevention, palliation, and/or treatment of cancer.

Cancers that can be treated by pharmaceutical compositions comprising the compounds of formula I or II either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macrophages and CD8+ T cells) or endothelial cells that may differentiate into blood vessel structures in the process of angiogenesis or vasculogenesis.

In another aspect of the invention, the pharmaceutical composition including the compounds of formula I or II is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor.

Additional cancers that can be treated by pharmaceutical compositions of the compounds of formula I or II include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The compounds of formula I or II can be used to treat cancer and to treat neurodegenerative disorders, auto-immune disorders, cardiovascular disorders, metabolic disorders, hamartoma syndrome, genetic muscle disorders, and myopathy. It is to be understood that each of the compounds of formulas I and II as recited herein are useful for a number of the above conditions, but not each and every compound is useful for each and every condition. It is well within the ability of those skilled in the art to easily determine which particular compound of formula I or II is useful for each particular condition without undue experimentation.

Further, compounds of formula I or II can be used as cytostatic adjuvants to most small molecule/chemotherapy regimens, but the compounds also can be used as single agents. The compounds of formulas I or II can thus be used in combination with other drugs.

Pharmaceutical Compositions, Routes of Administration, and Dosing

Provided is a pharmaceutical composition comprising a compound and a pharmaceutically acceptable carrier. The pharmaceutical composition can comprise a plurality of compounds and a pharmaceutically acceptable carrier. The pharmaceutical composition can comprise a pharmaceutically acceptable salt of a compound.

A pharmaceutical composition can further comprise at least one additional pharmaceutically active agent. The at least one additional pharmaceutically active agent can be an agent useful in the treatment of cancer or autophagy related diseases.

Pharmaceutical compositions can be prepared by combining one or more compounds with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound being administered, the size of the subject, or the severity of the disease or condition. One of ordinary skill in the art can empirically determine the effective amount of a particular compound and/or other therapeutic agent without necessitating undue experimentation. A maximum dose can be used, that is, the highest safe dose according to some medical judgment. Multiple doses per day can be contemplated to achieve appropriate systemic levels of compounds. Appropriate systemic levels can be determined by, for example, measurement of the patient's peak or sustained plasma level of the drug. "Dose" and "dosage" are used interchangeably herein. "Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by, and directly dependent on, the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds or an appropriate pharmaceutical composition thereof are effective, the compounds can be administered in an effective amount.

Generally, daily oral doses of a compound are, for human subjects, from about 0.01 milligrams/kg per day to 1,000 milligrams/kg per day. Oral doses in the range of 0.5 to 50 milligrams/kg, in one or more administrations per day, can yield therapeutic results. Dosage can be adjusted appropriately to achieve desired drug levels, local or systemic, depending upon the mode of administration. For example, intravenous administration can vary from one order to several orders of magnitude lower dose per day. If the response in a subject is insufficient at such doses, even higher doses (or effective higher doses by a different, more localized delivery route) can be employed to the extent that patient tolerance permits. Multiple doses per day are contemplated to achieve appropriate systemic levels of the compound.

For any compound the therapeutically effective amount can be initially determined from animal models. A therapeutically effective dose can also be determined from human data for compounds which have been tested in humans and for compounds which are known to exhibit similar pharmacological activities, such as other related active agents. Higher doses can be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

For clinical use, any compound can be administered in an amount equal or equivalent to 0.2-2,000 milligram (mg) of compound per kilogram (kg) of body weight of the subject per day. The compounds can be administered in a dose equal or equivalent to 2-2,000 mg of compound per kg body weight of the subject per day. The compounds can be administered in a dose equal or equivalent to 20-2,000 mg of compound per kg body weight of the subject per day. The compounds can be administered in a dose equal or equivalent to 50-2,000 mg of compound per kg body weight of the subject per day. The compounds can be administered in a dose equal or equivalent to 100-2,000 mg of compound per kg body weight of the subject per day. The compounds can be administered in a dose equal or equivalent to 200-2,000 mg of compound per kg body weight of the subject per day. Where a precursor or prodrug of a compound is to be administered, it is administered in an amount that is equivalent to, i.e., sufficient to deliver, the above-stated amounts of the compounds.

The formulations of the compounds can be administered to human subjects in therapeutically effective amounts. Typical dose ranges are from about 0.01 µg/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments can be used to optimize the dose and dosing frequency for any particular compound.

The compounds can be administered at a concentration in the range from about 0.001 µg/kg to greater than about 500 mg/kg. For example, the concentration can be 0.001 µg/kg, 0.01 µg/kg, 0.05 µg/kg, 0.1 µg/kg, 0.5 µg/kg, 1.0 µg/kg, 10.0 µg/kg, 50.0 µg/kg, 100.0 µg/kg, 500 µg/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed.

The compounds can be administered at a dosage in the range from about 0.2 mg/kg/day to greater than about 100 mg/kg/day. For example, the dosage can be 0.2 mg/kg/day to 100 mg/kg/day, 0.2 mg/kg/day to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 25 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 15 mg/kg/day, 2 mg/kg/day to 10 mg/kg/day, 2 mg/kg/day to 7.5 mg/kg/day, or 2 mg/kg/day to 5 mg/kg/day.

The compounds can be administered at a dosage in the range from about 0.25 mg/kg/day to about 25 mg/kg/day. For example, the dosage can be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/kg/day, 3.75 mg/kg/day, 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

The compound or precursor thereof can be administered in concentrations that range from 0.001 µM to greater than or equal to 500 µM. For example, the dose can be 0.001 µM, 0.01 µM, 0.02 µM, 0.05 µM, 0.1 µM, 0.15 µM, 0.2 M, 0.5 µM, 0.7 µM, 1.0 µM, 3.0 µM, 5.0 µM, 7.0 µM, 10.0 µM, 15.0 µM, 20.0 µM, 25.0 µM, 30.0 µM, 35.0 µM, 40.0 µM, 45.0 µM, 50.0 µM, 60.0 µM, 70.0 µM, 80.0 µM, 90.0 µM, 100.0 µM, 150.0 µM, 200.0 µM, 250.0 UM, 300.0 µM, 350.0 µM, 400.0 µM, 450.0 µM, to greater than about 500.0 µM or any incremental value thereof. It is to be understood that all values and ranges between these values and ranges are meant to be encompassed.

The compound or precursor thereof can be administered at concentrations that range from 0.10 µg/mL to 500.0 µg/mL. For example, the concentration can be 0.10 µg/mL, 0.50 µg/mL, 1 µg/mL, 2.0 µg/mL, 5.0 µg/mL, 10.0 µg/mL, 20 µg/mL, 25 µg/mL. 30 µg/mL, 35 µg/mL, 40 µg/mL, 45 µg/mL, 50 µg/mL, 60.0 µg/mL, 70.0 µg/mL, 80.0 µg/mL, 90.0 µg/mL, 100.0 µg/mL, 150.0 µg/mL, 200.0 µg/mL, 250.0 g/mL, 250.0 micro gram/mL, 300.0 µg/mL, 350.0 µg/mL, 400.0 µg/mL, 450.0 µg/mL, to greater than about 500.0 µg/mL or any incremental value thereof. It is to be understood that all values and ranges between these values and ranges are meant to be encompassed.

The formulations can be administered in pharmaceutically acceptable solutions, which can routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition can be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds to be formulated as tablets, pills, dragees, capsules, liquids, gels, syrups, slurries, suspensions, and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Optionally the oral formulations can also be formulated in saline solution or a buffer, e.g., EDTA, for neutralizing internal acid conditions or can be administered without any carriers.

Also contemplated are oral dosage forms of the compounds. The compounds can be chemically modified so that oral delivery of the derivative is efficacious. Generally, the chemical modification contemplated is the attachment of at least one moiety to the compound itself, where said moiety permits (a) inhibition of acid hydrolysis; and (b) uptake into the blood stream from the stomach or intestine. Also desired is the increase in overall stability of the compounds and increase in circulation time in the body. Examples of such moieties include polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts" In: Enzymes as Drugs, Hocenberg and Roberts, eds., Wiley-Interscience, New York, N. Y., pp. 367-383 (1981); Newmark et al., J Appl Biochem 4:185-189 (1982). Other polymers that could be used are poly-1,3-dioxolane and poly-1,3,6-tioxocane. For pharmaceutical usage, as indicated above, polyethylene glycol moieties are suitable.

The location of release of a compound can be the stomach, the small intestine (the duodenum, the jejunum, or the ileum), or the large intestine. One skilled in the art has available formulations which will not dissolve in the stomach yet will release the material in the duodenum or elsewhere in the intestine. The release can avoid the deleterious effects of the stomach environment, either by protection of the compound or by release of the compound beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit® L30D, Aquateric®, cellulose acetate phthalate (CAP), Eudragit® L, Eudragit® S, and shellac. These coatings can be used as mixed films.

A coating or mixture of coatings can also be used on tablets, which are not intended for protection against the stomach. This can include sugar coatings, or coatings which make the tablet easier to swallow. Capsules can consist of a hard shell (such as gelatin) for delivery of dry therapeutic (e.g., powder); for liquid forms, a soft gelatin shell can be used. The shell material of cachets could be thick starch or other edible paper. For pills, lozenges, molded tablets or tablet triturates, moist massing techniques can be used.

The therapeutic agent can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents can all be included. For example, the compound can be formulated (such as by liposome or microsphere encapsulation) and then further contained within an edible product, such as a refrigerated beverage containing colorants and flavoring agents.

One can dilute or increase the volume of the therapeutic with an inert material. These diluents could include carbohydrates, especially mannitol, a-lactose, anhydrous lactose, cellulose, sucrose, modified dextrans and starch. Certain inorganic salts can be also be used as fillers including calcium triphosphate, magnesium carbonate and sodium chloride. Some commercially available diluents are Fast-Flo®, Emdex®, STA-Rx 1500, Emcompress® and Avicel®.

Disintegrants can be included in the formulation of the therapeutic into a solid dosage form. Materials used as disintegrates include but are not limited to starch, including the commercial disintegrant based on starch, Explotab®. Sodium starch glycolate, AmberLite™ sodium carboxymethylcellulose, ultra-amylopectin, sodium alginate, gelatin, orange peel, acid carboxymethyl cellulose, natural sponge and bentonite can all be used. Another form of the disintegrant is the insoluble cationic exchange resin. Powdered gums can be used as disintegrants and as binders and these can include powdered gums such as agar, Karaya or tragacanth. Alginic acid and its sodium salt are also useful as disintegrants.

Binders can be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic agent.

An anti-frictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the therapeutic into the aqueous environment a surfactant might be added as a wetting agent. Surfactants can include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Microspheres formulated for oral administration can also be used. Such microspheres have been well defined in the art. All formulations for oral administration should be in dosages suitable for such administration.

For buccal administration, the compositions can take the form of tablets or lozenges formulated in conventional manner.

For topical administration, the compound can be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Nasal delivery of a pharmaceutical composition is also contemplated. Nasal delivery allows the passage of a pharmaceutical composition to the blood stream directly after administering the therapeutic product to the nose, without the necessity for deposition of the product in the lung. Formulations for nasal delivery include those with dextran or cyclodextran.

The compounds, when it is desirable to deliver them systemically, can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethylcellulose, sorbitol, or dextran. Optionally, the suspension can also contain suitable stabilizers or agents which increase the solubility of the compounds to allow for the preparation of highly concentrated solutions.

Alternatively, the active compounds can be in powder form for constitution with a suitable vehicle, e.g., sterile pyrogen-free water, before use.

The compounds can also be formulated in rectal or vaginal compositions such as suppositories or retention enemas, e.g., containing conventional suppository bases such as cocoa butter or other glycerides.

In addition to the formulations described above, a compound can also be formulated as a depot preparation. Such long-acting formulations can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro) capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, Science 249:1527-1533 (1990).

The compound and optionally one or more other therapeutic agents can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions contain an effective amount of a compound as described herein and optionally one or more other therapeutic agents included in a pharmaceutically acceptable carrier. The term "pharmaceutically acceptable carrier" means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also can be commingled with the compounds, and with each other, in a manner such that there is no interaction which would substantially impair the desired pharmaceutical efficiency.

The therapeutic agent(s), including specifically, but not limited to, a compound, can be provided in particles. "Particles" means nanoparticles or microparticles (or in some instances larger particles) which can consist in whole or in part of the compound or the other therapeutic agent(s) as described herein. The particles can contain the therapeutic agent(s) in a core surrounded by a coating, including, but not limited to, an enteric coating. The therapeutic agent(s) also can be dispersed throughout the particles. The therapeutic agent(s) also can be adsorbed into the particles. The particles can be of any order release kinetics, including zero-order release, first-order release, second-order release, delayed release, sustained release, immediate release, and any combination thereof, etc. The particle can include, in addition to the therapeutic agent(s), any of those materials routinely used in the art of pharmacy and medicine, including, but not limited to, erodible, non-erodible, biodegradable, or nonbiodegradable material or combinations thereof. The particles can be microcapsules which contain the compound in a solution or in a semi-solid state. The particles can be of virtually any shape.

Both non-biodegradable and biodegradable polymeric materials can be used in the manufacture of particles for delivering the therapeutic agent(s). Such polymers can be natural or synthetic polymers. The polymer is selected based on the period of time over which release is desired. Bioadhesive polymers of particular interest include bioerodible hydrogels described in Sawhney et al., Macromolecules 26:581-587 (1993), the teachings of which are specifically incorporated by reference herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) can be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that can result in substantially constant blood levels of a drug over an extended time period. The term "delayed release" is used in its conventional sense to refer to a drug formulation in which there is a time delay between administration of the formulation and the release of the drug there from. "Delayed release" can or cannot involve gradual release of drug over an extended period of time, and thus can or cannot be "sustained release."

Use of a long-term sustained release implant can be particularly suitable for treatment of chronic conditions. "Long-term" release means that the implant is constructed and arranged to deliver therapeutic levels of the active ingredient for at least 7 days, and up to 30-60 days. Long-term sustained release implants are well-known to those of ordinary skill in the art and include some of the release systems described above.

Certain Definitions

For convenience, some terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The phrase "and/or," in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, to A only (optionally including elements other than B); or to B only (optionally including elements other than A); or yet, to both A and B (optionally including other elements); etc.

In the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

In the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, to at least one, optionally including more than one, A, with no B present (and optionally including elements other than B); or to at least one, optionally including more than one, B, with no A present (and optionally including elements other than A); or yet, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

The term "chiral" refers to molecules which have the property of non-superimposability of the mirror image partner, while the term "achiral" refers to molecules which are superimposable on their mirror image partner. "*" depicts certain chiral centers.

The term "stereoisomers" refers to compounds which have identical chemical constitution but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds, John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or I meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Various compounds contained in compositions can exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms can be present in a substituent such as an alkyl group. All such isomers, as well as mixtures thereof, are intended to be included in this disclosure.

If, for instance, a particular enantiomer of compound is desired, it can be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well-known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this disclosure.

The phrase "pharmaceutically acceptable excipient" or "pharmaceutically acceptable carrier" means a pharmaceutically acceptable material, composition or vehicle, such as a liquid or solid filler, diluent, excipient, solvent or encapsulating material, involved in carrying or transporting the subject chemical from one organ or portion of the body to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Pharmaceutical compositions are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", J. Pharm. Sci. 66:1-19.)

In other cases, the compounds useful in the methods can contain one or more acidic functional groups and, thus, can form pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prodrug" as used herein encompasses compounds that, under physiological conditions, are converted into therapeutically active agents. A common method for making a prodrug is to include selected moieties that are hydrolyzed under physiological conditions to reveal the desired molecule. The prodrug can be converted by an enzymatic activity of the host animal.

The term "prophylactic or therapeutic" treatment is art-recognized and includes administration to the patient of one or more compound of the disclosure. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" or "subject" refers to a mammal suffering of a disease, disorder, or condition. A patient or subject can be a primate, canine, feline, or equine. A patient or subject can be a bird. The bird can be a domesticated bird, such as chicken. The bird can be a fowl. A patient or subject can be a human.

An aliphatic chain comprises the classes of alkyl, alkenyl and alkynyl defined below. A straight aliphatic chain is limited to unbranched carbon chain moieties. The term "aliphatic group" refers to a straight chain, branchedchain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. A straight chain or branched chain alkyl can have 30 or fewer carbon atoms in its backbone (e.g., $C_1$-$C_{30}$ for straight chains, $C_3$-$C_{30}$ for branched chains), or 20 or fewer. Alkyl groups can be substituted or unsubstituted. The term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —$(CH_2)$—, ethylene —$(CH_2CH_2)$—, n-propylene —$(CH_2CH_2CH_2)$—, isopropylene —$(CH_2CH(CH_3))$—, and the like. Alkylene groups can be cyclic or acyclic, branched or unbranched carbon chain moiety, and can be optionally substituted with one or more substituents.

"Cycloalkyl" means mono- or bicyclic or bridged or spirocyclic, or polycyclic saturated carbocyclic rings, each having from 3 to 12 carbon atoms. In various aspects, cycloalkyls have from 3-10 carbon atoms in their ring structure, or 3-6 carbons in the ring structure. Cycloalkyl groups can be substituted or unsubstituted.

Unless the number of carbons is otherwise specified, "lower alkyl," means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. A substituent designated herein as alkyl can be a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl but having one or more triple bonds in the moiety.

The term "alkylthio" refers to an alkyl group, as defined above, having a sulfur moiety attached thereto. The "alkylthio" moiety can be represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like. The terms "alkoxyl" or "alkoxy" refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_{10}$, where m and $R_{10}$ are described below.

The terms "amine" and "amino" are art-recognized and refer to both unsubstituted and substituted amines, e.g., a moiety that can be represented by the formulae:

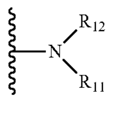

wherein $R_{11}$ and $R_{12}$ each independently represent a hydrogen, an alkyl, an alkenyl, —$(CH_2)_m$—$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In some instances, only one of $R_{11}$ or $R_{12}$ can be a carbonyl, e.g., $R_{11}$, $R_{12}$, and the nitrogen together do not form an imide. $R_{11}$ and $R_{12}$ each independently can represent a hydrogen, an alkyl, an alkenyl, or $—(CH_2)_m—R_{10}$. Thus, the term "alkylamine" means an amine group, as defined above, having a substituted or unsubstituted alkyl attached thereto, i.e., at least one of $R_{11}$ and $R_{12}$ is an alkyl group. An amino group or an alkylamine is basic, meaning it has a conjugate acid with a $pK_a$>7.00, i.e., the protonated forms of these functional groups have $pK_a$s relative to water above about 7.00.

The term "amide" refers to a group

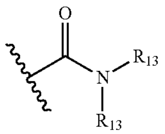

wherein each $R_{13}$ independently represent a hydrogen or hydrocarbyl group, or two $R_{13}$ are taken together with the N atom to which they are attached complete a heterocycle having from 4 to 8 atoms in the ring structure.

The term "aryl" includes 3- to 12-membered substituted or unsubstituted single-ring aromatic groups in which each atom of the ring is carbon (i.e., carbocyclic aryl) or where one or more atoms are heteroatoms (i.e., heteroaryl). In various aspects, aryl groups include 5- to 12-membered rings, or 6- to 10-membered rings. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, 5- to 12-membered rings, or 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. Each instance of an aryl group can be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring can be substituted at one or more ring positions with one or more substituents, such as halogen, azide, alkyl, aryl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, the aryl group can be an unsubstituted $C_5$-$C_{12}$ aryl or a substituted $C_5$-$C_{10}$ aryl.

The term "halo", "halide", or "halogen" means halogen and includes, for example, and without being limited thereto, fluoro, chloro, bromo, iodo and the like, in both radioactive and non-radioactive forms. Halo can be selected from the group consisting of fluoro, chloro and bromo.

The terms "heterocyclyl" or "heterocyclic group" refer to 3- to 12-membered ring structures, 5- to 12-membered rings, or 5- to 10-membered rings, whose ring structures include one to four heteroatoms. Heterocycles can be monocyclic, bicyclic, spirocyclic, or polycyclic. Heterocycles can be saturated or unsaturated. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aryl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, $—CF_3$, —CN, and the like.

The term "carbonyl" is art-recognized and includes such moieties as can be represented by the formula:

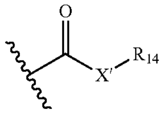 or 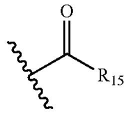

wherein X' is a bond or represents an oxygen, a nitrogen, or a sulfur, and $R_{14}$ represents a hydrogen, an alkyl, an alkenyl, $—(CH_2)_m—R_{10}$ or a pharmaceutically acceptable salt, $R_{15}$ represents a hydrogen, an alkyl, an alkenyl or $—(CH_2)_m—R_{10}$, where m and $R_{10}$ are as defined above. Where X' is an oxygen and $R_{14}$ or $R_{15}$ is not hydrogen, the formula represents an "ester." Where X' is an oxygen, and $R_{14}$ is as defined above, the moiety is referred to herein as a carboxyl group, and particularly when $R_{14}$ is a hydrogen, the formula represents a "carboxylic acid". Where X' is an oxygen, and $R_{15}$ is a hydrogen, the formula represents a "formate." In general, where the oxygen atom of the above formula is replaced by a sulfur, the formula represents a "thiocarbonyl" group. Where X' is a sulfur and $R_{14}$ or $R_{15}$ is not hydrogen, the formula represents a "thioester" group. Where X' is a sulfur and $R_{14}$ is a hydrogen, the formula represents a "thiocarboxylic acid" group. Where X' is a sulfur and $R_{15}$ is a hydrogen, the formula represents a "thioformate" group. On the other hand, where X' is a bond, and $R_{14}$ is not hydrogen, the above formula represents a "ketone" group. Where X' is a bond, and $R_{14}$ is a hydrogen, the above formula represents an "aldehyde" group.

The term "nitro" means-$NO_2$; the term "sulfhydryl" means —SH; the term "hydroxyl" means —OH; the term "sulfonyl" means $—SO_2—$; the term "azido" means $—N_3$; the term "cyano" means —CN; the term "isocyanato" means-NCO; the term "thiocyanato" means —SCN; the term "isothiocyanato" means —NCS; and the term "cyanato" means —OCN.

The definition of each expression, e.g., alkyl, m, n, etc., when it occurs more than once in any structure, is intended to be independent of its definition elsewhere in the same structure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. The term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. Heteroatoms such as nitrogen can have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl, or an aromatic or heteroaromatic moiety. The substituents on substituted alkyls can be selected from $C_{1-6}$ alkyl, $C_3$-6 cycloalkyl, halogen, carbonyl, cyano, or hydroxyl. The substituents on substituted alkyls can be selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "substituted" as used herein also refers to a group that is substituted with one or more groups including, but not limited to, the following groups: halogen (e.g., F, Cl, Br, and I), R, OR, ROH (e.g., $CH_2OH$), $OC(O)N(R)_2$, CN, NO, $NO_2$, $ONO_2$, azido, $CF_3$, $OCF_3$, methylenedioxy, ethylenedioxy, ($C_3$-$C_{20}$) heteroaryl, $N(R)_2$, $Si(R)_3$, SR, SOR, $SO_2R$, $SON(R)_2$, $SO_3R$, $P(O)(OR)_2$, $OP(O)(OR)_2$, C(O)R, C(O)C(O)R, $C(O)CH_2C(O)R$, C(S)R, C(O)OR, OC(O)R, $C(O)N(R)_2$, C(O)N(R)OH, $OC(O)N(R)_2$, $C(S)N(R)_2$, $(CH_2)_{0-2}N(R)C(O)R$, $(CH_2)_{0-2}N(R)N(R)_2$, N(R)N(R)C(O) R, N(R)N(R)C(O)OR, $N(R)N(R)CON(R)_2$, N(R) $SO_2R$, N(R) $SON(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, or C(=NOR) R wherein R can be hydrogen, ($C_1$-$C_{20}$)alkyl, ($C_6$-$C_{20}$) aryl, heterocyclyl or polyalkylene oxide groups, such as polyalkylene oxide groups of the formula $—(CH_2CH_2O)_f—R—OR$, $—(CH_2CH_2CH_2O)_g—R—OR$, $—(CH_2CH_2O)_f(CH_2CH_2CH_2O)_g—R—OR$ each of which can, in turn, be substituted or unsubstituted and wherein f and g are each independently an integer from 1 to 50 (e.g., 1 to 10, 1 to 5, 1 to 3 or 2 to 5). Substituted also includes a group that is substituted with one or more groups including, but not limited to, the following groups: fluoro, chloro, bromo, iodo, amino, amido, alkyl, hydroxy, alkoxy, alkylamido, alkenyl, alkynyl, alkoxycarbonyl, acyl, formyl, arylcarbonyl, aryloxycarbonyl, aryloxy, Boc, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement.

Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

The chemical elements are identified in accordance with the Periodic Table of the Elements, CAS version, Handbook of Chemistry and Physics, 67th Ed., 1986-87, inside cover.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein can be suitably practiced in the absence of any element(s) or limitation(s), which is/are not specifically disclosed herein. Thus, for example, each instance herein of any of the terms "comprising," "consisting essentially of," and "consisting of" can be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It will be understood by one of ordinary skill in the relevant arts that other suitable modifications and adaptations to the compositions and methods described herein are readily apparent from the description of the disclosure contained herein in view of information known to the ordinarily skilled artisan and can be made without departing from the scope of the disclosure. Having now described the present disclosure in detail, the same will be more clearly understood by reference to the following examples, which are included herewith for purposes of illustration only and are not intended to be limiting of the disclosure.

EXAMPLES

The present invention can be better understood by reference to the following examples which are offered by way of illustration. The present invention is not limited to the examples given herein.

Synthetic Procedures

Chemical Preparation

Materials and Methods

All commercial reagents and solvents were used as received. Anhydrous solvents were dried over 4 A° molecular sieves. Thin layer chromatography was performed on silica gel 60G F254 glass plates. 1H NMR spectra were recorded on an Agilent VXR (500 MHZ). 1H NMR data are reported as follows: chemical shift, multiplicity (br=broad, s=singlet, d=doublet, t=triplet, q=quartet, m=multiplet) coupling constants and integration. Chemical shifts are reported in parts per million (ppm). Purity for final compounds is greater than 95% unless otherwise noted and was measured using Agilent 1100 series high performance liquid chromatography (HPLC) systems with UV detection at 254 nm. High resolution mass spectra were recorded with a Waters G2-XS QT of using an electrospray ionization mode (ESI).

Experimental Procedures

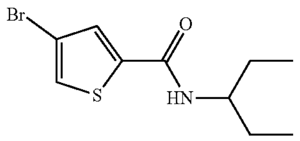

4-bromo-N-(pentan-3-yl)thiophene-2-carboxamide

To a solution of 4-bromothiophene-2-carboxylic acid (5.0 g, 24.16 mmol) in dimethylformamide (120 mL), under an argon atmosphere, was added Bis(2-oxo-3-oxazolidinyl) phosphinic chloride (7.40 g, 29.1 mmol) and the mixture was stirred at room temperature for 10 minutes. Diisopropyl ethyl amine (10 mL, 72.5 mmol) was then added to the reaction mixture and stirred was at room temperature for 20 minutes. A solution of 3-amino pentane (5.3 g, 60.4 mmol) in dimethylformamide (5 mL) was then slowly added, in dropwise fashion, (Exothermic) and monitored by thin layer chromatography (16 hours). Upon completion, the reaction was diluted with ethyl acetate and washed subsequently with water (5×20 mL) and saturated aqueous sodium chloride (2×20 mL). The organic layer was dried with sodium sulfate, filtered, and concentrated in vacuo. The resulting solid residue was purified via medium pressure liquid chromatography ($SiO_2$, 100% hexanes to 10% ethyl acetate/hexanes) to provide the title compound (6.2 g, 93% yield). 1H NMR (500 MHZ, Chloroform-d) δ 7.37 (p, J=1.5 Hz, 2H), 5.72 (d, J=9.0 Hz, 1H), 3.95 (dtt, J=9.0, 7.9, 5.3 Hz, 1H), 1.71-1.59 (m, 2H), 1.54-1.41 (m, 2H), 0.95 (t, J=7.4 Hz, 6H).

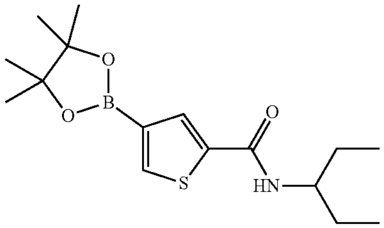 [SMILES: CCC(CC)NC(=O)c1cc(B2OC(C)(C)C(C)(C)O2)cs1]

4-pinacolborane-N-(pentan-3-yl)thiophene-2-carboxamide

A mixture of 4-bromo-N-(pentan-3-yl)thiophene-2-carboxamide (6.20 g, 22.5 mmol), Bis(pinacolato)diboron (8.60 g, 33.7 mmol), 1,1'-bis(diphenylphosphino) ferrocene (0.39 g, 0.7 mmol), and potassium acetate (6.70 g, 67.5 mmol) in dioxane/ethanol (10:1, 113 mL) was sparged for 20 minutes with argon gas then treated with 1,1'-bis(diphenylphosphino) ferrocene-palladium (II) dichloride dichloromethane (0.56 g, 0.70 mmol). The mixture was sealed under an atmosphere of argon and heated to 110° C. and monitored by thin layer chromatography (16 hours). Upon completion, the mixture was cooled to room temperature and diluted with ethyl acetate. The mixture was filtered through a small pad of Celite (5 cm) and the pad washed again with ethyl acetate (20 mL). The combined filtrates were then washed with water (3×20 mL) and then saturated aqueous sodium chloride (2×20 mL). The organic layer was dried with sodium sulfate, filtered, and concentrated in vacuo. The resulting solid residue was purified via medium pressure liquid chromatography ($SiO_2$, 100% hexanes to 30% ethyl acetate/hexanes) to provide the title compound (6.20 g, 85% yield). 1H NMR (500 MHZ, Chloroform-d) δ 8.01 (d, J=1.1 Hz, 1H), 7.66 (d, J=1.1 Hz, 1H), 5.72 (d, J=9.1 Hz, 1H), 4.02-3.91 (m, 1H), 1.72-1.58 (m, 2H), 1.53-1.39 (m, 2H), 1.35 (s, 12H), 0.94 (t, J=7.5 Hz, 6H).

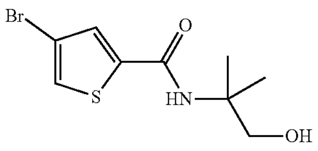

4-bromo-N-(1-hydroxy-2-methylpropan-2-yl)thiophene-2-carboxamide

To a solution of 4-bromothiophene-2-carboxylic acid (1.0 g, 4.9 mmol) in dimethylformamide (25 mL), under an argon atmosphere was added Bis(2-oxo-3-oxazolidinyl)phosphinic chloride, (1.48 g, 5.81 mmol) and the mixture stirred at room temperature for 10 minutes. Diisopropyl ethyl amine (2.50 mL, 14.6 mmol) was then added and stirred at room temperature for 20 minutes. A solution of 2-amino-2-methyl-1-propanol (1.10 g, 12.1 mmol) in dimethylformamide (2.0 mL) was then added dropwise (Exothermic) and monitored by thin layer chromatography (16 hours). Upon completion, the mixture was diluted with ethyl acetate and washed with water (5×10 mL) and saturated aqueous sodium chloride (2×10 mL). The organic layer was dried with sodium sulfate, filtered, and concentrated in vacuo. The resulting solid residue was purified via medium pressure liquid chromatography ($SiO_2$, 100% hexanes to 10% ethyl acetate/hexanes) to provide the title compound (1.3 g, 97% yield). 1H NMR (500 MHZ, Chloroform-d) δ 7.43-7.35 (s, 1H), 7.33 (s, 1H), 6.07 (s, 1H), 3.68 (s, 2H), 1.40 (s, 6H).

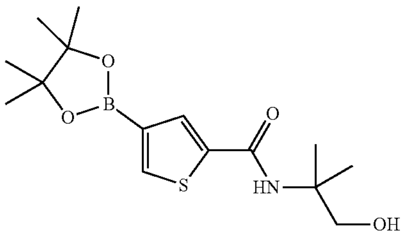 [SMILES: CC(C)(CO)NC(=O)c1cc(B2OC(C)(C)C(C)(C)O2)cs1]

4-pinacolborane-N-(1-hydroxy-2-methylpropan-2-yl)thiophene-2-carboxamide

A mixture of 4-bromo-N-(1-hydroxy-2-methylpropan-2-yl)thiophene-2-carboxamide (1.36 g, 4.90 mmol), Bis(pinacolato)diboron (1.87 g, 7.40 mmol), 1,1'-bis(diphenylphosphino) ferrocene (0.14 g, 0.25 mmol), and potassium acetate (1.50 g, 14.70 mmol) in dioxane/ethanol (10:1, 22.0 mL) was sparged for 20 minutes with argon. 1,1'-bis(diphenylphosphino) ferrocene-palladium (II) dichloride dichloromethane (0.21 g, 0.25 mmol) was added and the mixture, under an argon atmosphere, was heated to 110° C. Upon completion, the mixture was cooled to room temperature and diluted with ethyl acetate. The mixture was filtered through a small pad of Celite (5 cm) and the pad washed with additional ethyl acetate (20 mL). The combined filtrates were washed subsequently with water (3×20 mL) and saturated aqueous sodium chloride (2×20 mL). The organic layer was dried with sodium sulfate, filtered, and concentrated in vacuo. The resulting solid residue was purified via medium pressure liquid chromatography ($SiO_2$, 100% hexanes to 40% ethyl acetate/hexanes) to provide the title compound (1.40 g, 86% yield). 1H NMR (500 MHZ, Chloroform-d) δ 8.03 (s, 1H), 7.65 (s, 1H), 6.10 (s, 1H), 3.69 (s, 2H), 1.40 (s, 6H), 1.35 (s, 12H).

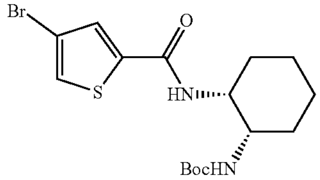 [SMILES: CC(C)(C)OC(=O)N[C@H]1CCCC[C@H]1NC(=O)c1cc(Br)cs1]

tert-butyl [(1S,2R)-2-{[(4-bromothiophen-2-yl) carbonyl]amino}cyclohexyl]carbamate To a solution of 4-bromothiophene-2-carboxylic acid (1.04 g, 5.00 mmol) in dimethylformamide (25 mL), under an argon atmosphere, was treated with bis(2-oxo-3-oxazolidinyl)phosphinic chloride (1.6 g, 6.0 mmol) and the mixture stirred at room temperature for 10 minutes. Diisopropylethyl amine (2.60 mL, 15.0 mmol) was then added stirred for 20 minutes. A solution of tert-butyl [(1S,2R)-2-amino-cyclohexyl]carbamate (1.60 g, 7.50 mmol) in dimethylformamide (2.0 mL) was then slowly added dropwise (Exothermic) and monitored by thin layer chromatography (16 hours). Upon completion, the mixture was diluted with ethyl acetate and washed with water (5×10 mL) and saturated aqueous sodium chloride (2×10 mL). The organic layer was dried with sodium sulfate, filtered, and concentrated in vacuo. The resulting solid residue was purified via medium pressure liquid chromatography ($SiO_2$, 100% hexanes to 10% ethyl acetate/hexanes) to provide the title compound (1.80 g, 89% yield). 1H NMR (500 MHZ, Chloroform-d) δ 7.80 (s, 1H), 7.39 (d, J=1.4 Hz, 1H), 7.34 (d, J=1.4 Hz, 1H), 4.92 (d, J=7.3 Hz, 1H), 4.02-3.82 (m, 2H), 1.78-1.75 (m, 2H), 1.66-1.58 (m, 2H), 1.51 (s, 9H), 1.45 (m, 4H).

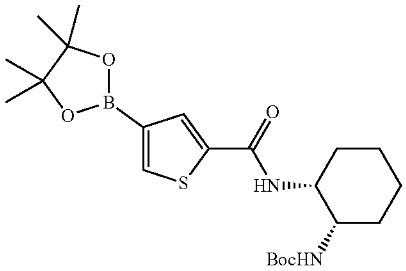 [SMILES: CC(C)(C)OC(=O)N[C@H]1CCCC[C@H]1NC(=O)c1cc(B2OC(C)(C)C(C)(C)O2)cs1]

4-pinacolborane-tert-butyl {(1S,2R)-2-[(thiophenyl-carbonyl)amino]cyclohexyl}carbamate A mixture of tert-butyl [(1S,2R)-2-{[(4-bromothiophen-2-yl) carbonyl]amino}cyclohexyl]carbamate (1.22 g, 3.03 mmol), bis(pinacolato)diboron (1.16 g, 4.55 mmol), 1,1'-bis (diphenylphosphino) ferrocene (89.0 mg, 0.16 mmol), and potassium acetate (0.90 g, 9.10 mmol) in dioxane/ethanol (10:1, 15 mL) was sparged for 20 minutes with argon gas (bubbling in the mixture). 1,1'-bis(diphenylphosphino) ferrocene-palladium (II) dichloride dichloromethane (0.13 g, 0.16 mmol) was then added, sealed under an atmosphere of argon, and heated to 110° C. (12 hours). Upon completion, the mixture was cooled and diluted with ethyl acetate. The mixture was filtered through a small pad of Celite (5 cm) and the pad washed with additional ethyl acetate (20 mL). The combined filtrates were washed with water (3×20 mL) and saturated aqueous sodium chloride (2×20 mL). The organic layer was then dried with sodium sulfate, filtered, and concentrated in vacuo. The resulting residue was purified via medium pressure liquid chromatography ($SiO_2$, 100% hexanes to 70% ethyl acetate/hexanes to provide the title compound (1.10 g, 80% yield). 1H NMR (500 MHZ, Chloroform-d) δ 8.02 (s, 1H), 7.72 (s, 1H), 4.94 (m, 1H), 4.23-3.84 (m, 2H), 2.22-1.93 (m, 2H), 1.90-1.63 (m, 2H), 1.49 (s, 9H), 1.31 (s, 12H), 1.24 (m, 4H).

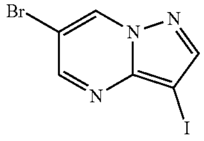 [SMILES: Brc1cnc2c(I)cnn2c1]

6-bromo-3-iodopyrazolo[1,5-a]pyrimidine

To a stirred solution of 6-bromopyrazolo[1,5-a]pyrimidine (1.00 g, 5.05 mmol) in dimethylformamide (50 mL), under argon atmosphere, was added N-iodosuccinimide (1.20 g, 5.31 mmol) portion-wise during 20 minutes. The resulting solution stirred at room temperature until completion (4 hours). The mixture was then diluted with ethyl acetate and washed with water (5×20 mL) and saturated aqueous sodium thiosulfate (2×20 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes to provide the title compound (1.52 g, 93% yield). 1H NMR (500 MHZ, Chloroform-d) δ 8.82 (d, J=2.1 Hz, 1H), 8.54 (d, J=2.1 Hz, 1H), 8.12 (s, 1H).

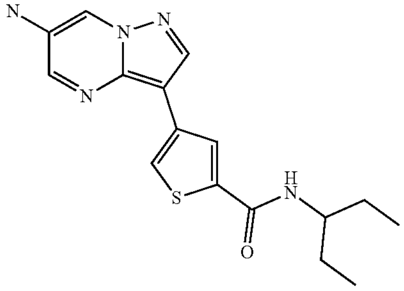 [SMILES: CCC(CC)NC(=O)c1cc(-c2cnn3cc(N)cnc23)cs1]

4-(6-bromopyrazolo[1,5-a]pyrimidin-3-yl)-N-(pentan-3-yl)thiophene-2-carboxamide

A mixture of 6-bromo-3-iodopyrazolo[1,5-a]pyrimidine (1.30 g, 4.15 mmol), 4-pinacolborane-N-(pentan-3-yl)thiophene-2-carboxamide (1.30 g, 4.15 mmol) and potassium phosphate (2.70 g, 12.5 mmol), in dioxane/water (10:1, 42 mL), was sparged for 20 minutes with argon gas (bubbling into the mixture). Tetrakis(triphenylphosphine) palladium (0)(0.024 g, 0.21 mmol) was then added and sealed under an atmosphere of argon, then heated to 110° C. (16 hours). Upon completion, the reaction was cooled to room temperature and diluted with ethyl acetate. The mixture was filtered through a small pad of Celite (5 cm) and the pad washed with additional ethyl acetate (20 mL). The filtrate was then washed with water (3×20 mL) and saturated aqueous sodium chloride (2×20 mL). The organic layer was dried with sodium sulfate, filtered, and concentrated in vacuo. The resulting residue was purified via medium pressure liquid chromatography ($SiO_2$, 100% hexanes to 40% ethyl acetate/hexanes to provide the title compound (1.34 g, 82% yield). 1H NMR (500 MHZ, DMSO-$d_6$) δ 9.64 (d, J=2.2 Hz, 1H), 8.73 (d, J=2.2 Hz, 1H), 8.59 (s, 1H), 8.35 (d, J=1.3 Hz, 1H), 8.18 (d, J=8.7 m, Hz, 1H), 8.15-8.08 (m, 1H), 3.78-3.68 (m, 1H), 1.61-1.39 (m, 4H), 0.86 (t, J=7.4 Hz, 6H). HRMS (ESI) m/z calculated for $C_{16}H_{18}BrN_4OS$ [M+H], 393.0385; found 393.0391. HPLC purity (AUC): 96.3%

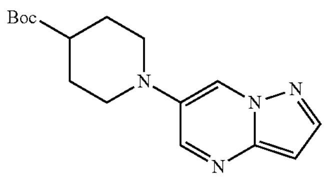 [SMILES: CC(C)(C)OC(=O)C1CCN(c2cnc3ccnn3c2)CC1]

tert-butyl 4-(pyrazolo[1,5-a]pyrimidin-6-yl) piperazine-1-carboxylate

To a stirred solution of 6-bromopyrazolo[1,5-a]pyrimidine (2.0 g, 10.11 mmol), tert-butyl piperazine-1-carboxylate (5.70 g, 30.31 mmol) in DMSO (100 mL) under argon atmosphere was added p-toluene sulfonic acid monohydrate (2.20 g, 11.13 mmol) and the mixture heated to 120° C. (18 hours). Upon completion, the mixture was cooled to room temperature, diluted with ethyl acetate, and washed with aqueous sodium bicarbonate (3×100 mL) and water (2×100 mL). The organic layer was dried with sodium sulfate, filtered, and concentrated in vacuo. The resulting residue was purified via medium pressure liquid chromatography ($SiO_2$, 100% hexanes to 70% ethyl acetate/hexanes) to provide tert-butyl 4-(pyrazolo[1,5-a]pyrimidin-6-yl) piperazine-1-carboxylate (2.15 g, 70% yield). 1H NMR (500 MHZ, Chloroform-d) δ 8.46 (d, J=2.6 Hz, 1H), 8.18-8.12 (m, 1H), 8.00 (d, J=2.4 Hz, 1H), 6.64 (dd, J=2.4, 0.8 Hz, 1H), 3.64 (t, J=5.1 Hz, 4H), 3.06 (t, J=5.1 Hz, 4H), 1.49 (s, 9H).

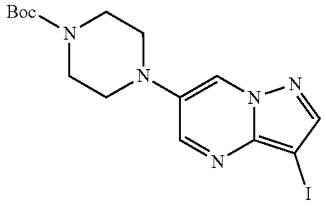 [SMILES: CC(C)(C)OC(=O)N1CCN(c2cnc3c(I)cnn3c2)CC1]

tert-butyl 4-(3-iodopyrazolo[1,5-a]pyrimidin-6-yl) piperazine-1-carboxylate

To a stirred solution of tert-butyl 4-(pyrazolo[1,5-a]pyrimidin-6-yl) piperazine-1-carboxylate (0.25 g, 0.83 mmol) in dimethylformamide (8.0 mL) at room temperature (argon atmosphere) was slowly added N-iodosuccinamide (0.21 g, mmol) portion-wise during 10 minutes. The resulting mixture was stirred at room temperature and monitored by thin layer chromatography (4 hours). Upon completion, the mixture was diluted with ethyl acetate and washed with water (5×5 mL) and saturated aqueous sodium thiosulfate (2×5 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes) to provide tert-butyl 4-(3-iodopyrazolo[1,5-a]pyrimidin-6-yl) piperazine-1-carboxylate (0.34 g, 94% yield). 1H NMR (500 MHZ, Chloroform-d) δ 8.51 (d, J=2.5 Hz, 1H), 8.12 (d, J=2.6 Hz, 1H), 8.02 (s, 1H), 3.65 (t, J=5.1 Hz, 4H), 3.07 (t, J=5.0 Hz, 4H), 1.49 (s, 9H).

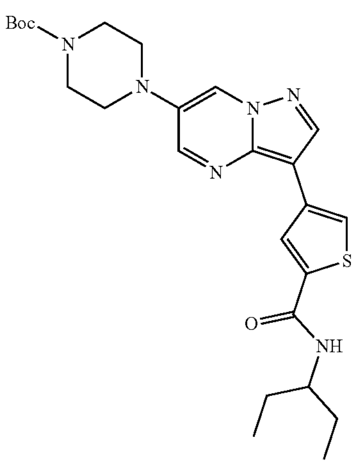 [SMILES: CCC(CC)NC(=O)c1cc(-c2cnn3cc(N4CCN(C(=O)OC(C)(C)C)CC4)cnc23)cs1]

tert-butyl 4-(3-{5-[(pentan-3-yl) carbamoyl]thiophen-3-yl}pyrazolo[1,5-a]pyrimidin-6-yl) piperazine-1-carboxylate A mixture of tert-butyl 4-(3-iodopyrazolo[1,5-a]pyrimidin-6-yl) piperazine-1-carboxylate (0.16 g, 0.38 mmol), 4-pinacolborane-N-(pentan-3-yl)thiophene-2-carboxamide (0.24 g, 0.75 mmol), potassium phosphate (0.25 g, 1.14 mmol), in dioxane/water (10:1, 4.0 mL) was sparged for 20 minutes with argon gas (bubbling into the mixture).

Tetrakis(triphenylphosphine) palladium (0)(44.0 mg, 0.04 mmol) was then added and the mixture was sealed (argon atmosphere) and heated to 110° C. using a Anton-Parr microwave monowave reactor (12 hours). Upon completion, the mixture was diluted with ethyl acetate. The filtered through a small pad of Celite (5 cm) and the pad washed with additional ethyl acetate (10 mL). The combined filtrates were washed with water (3×10 mL) and saturated aqueous sodium chloride (2×10 mL). The organic layer was then dried with sodium sulfate, filtered, and concentrated in vacuo. The resulting residue was purified via reverse phase column chromatography via medium pressure liquid chromatography ($C_{18}$, 100% ammonium formate to 40% methanol/ammonium formate). Fractions that containing the desired product were combined and the volatiles concentrated in vacuo. The water/residue mixture was extracted with ethyl acetate (4×20 mL). The organic layer was dried with sodium sulfate, filtered, and concentrated in vacuo (0.15 g, 79% yield). 1H NMR (500 MHZ, Chloroform-d) δ 8.53 (d, J=2.6 Hz, 1H), 8.25 (s, 1H), 8.13 (d, J=2.6 Hz, 1H), 8.02 (d, J=1.4 Hz, 1H), 7.95 (d, J=1.4 Hz, 1H), 5.74 (d, J=9.1 Hz, 1H), 4.06-3.98 (m, 1H), 3.66 (q, J=8.1, 6.6 Hz, 4H), 3.09 (d, J=5.4 Hz, 4H), 1.75-1.61 (m, 2H), 1.55-1.52 (m, 2H), 1.51 (s, 9H), 0.99 (t, J=7.4 Hz, 6H). HRMS (ESI) m/z calculated for $C_{25}H_{34}N_6NaO_3S$ [M+Na], 521.2311; found 521.2311. HPLC purity (AUC): 98.6%.

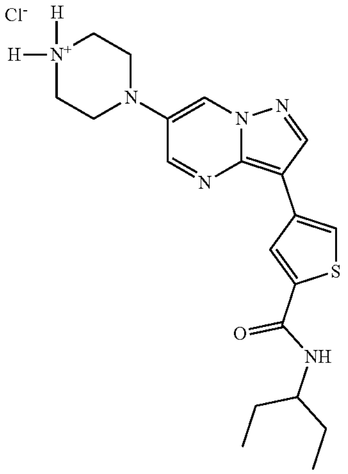 [SMILES: [Cl-] ; CCC(CC)NC(=O)c1cc(-c2cnn3cc(N4CC[NH2+]CC4)cnc23)cs1]

2-(diethylamino)-1-{4-[6-(piperazin-1-yl) pyrazolo[1,5-a]pyrimidin-3-yl]thiophen-2-yl}ethan-1-one hydrochloride A mixture of 4-(6-bromopyrazolo[1,5-a]pyrimidin-3-yl)-N-(pentan-3-yl)thiophene-2-carboxamide (0.030 g, 0.061 mmol) in methanol (2.0 mL) was treated dropwise with hydrochloric acid (4.0 N in dioxane, 0.15 mL, 0.61 mmol). The mixture was stirred at room temperature, under an argon atmosphere, for 2 hours and concentrated in vacuo to provide the product as an HCl salt (25.0 mg, 100% yield). 1H NMR (500 MHZ, Methanol-$d_4$) δ 8.72 (d, J=2.6 Hz, 1H), 8.52 (d, J=2.6 Hz, 1H), 8.38 (s, 1H), 8.32 (d, J=1.4 Hz, 1H), 8.12 (d, J=1.3 Hz, 1H), 3.88 (tt, J=8.7, 5.0 Hz, 1H), 3.78-3.71 (m, 2H), 3.69-3.67 (m, 2H), 3.59 (m, 2H), 3.46 (m, 2H), 1.77-1.58 (m, 2H), 1.63-1.51 (m, 2H), 0.98 (t, J=7.4 Hz, 6H). HRMS (ESI) m/z calculated for $C_{20}H_{27}N_6OS$ [M+H], 399.1967; found 399.1963. HPLC purity (AUC): 97.2%.

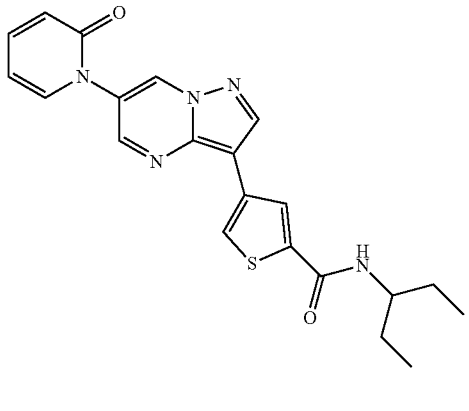 [SMILES: CCC(CC)NC(=O)c1cc(-c2cnn3cc(-n4ccccc4=O)cnc23)cs1]

4-[6-(2-oxo-1,2-dihydropyridin-1-yl) pyrazolo[1,5-a]pyrimidin-3-yl]-N-(pentan-3-yl)thiophene-2-carboxamide A mixture of 4-(6-bromopyrazolo[1,5-a]pyrimidin-3-yl)-N-(pentan-3-yl)thiophene-2-carboxamide (0.095 g, 0.25 mmol), 2-hydroxypyridine (0.069 g, 0.73 mmol), and potassium carbonate (0.10 g, 0.73 mmol), in dimethylformamide (2.0 mL), was sparged for 20 minutes with argon gas (bubbling into the mixture). Copper (I) iodide (0.015 g, 0.08 mmol) was added, and the mixture heated to 110° C. using an Anton-Parr monowave microwave reactor (12 hours). Upon completion, the reaction was cooled to room temperature and diluted with ethyl acetate. The mixture was filtered through a small pad of Celite (5 cm) and the pad washed with additional ethyl acetate (10 mL). The combined filtrates were washed with water (5×10 mL) and saturated aqueous sodium chloride (2×10 mL). The organic layer was dried with sodium sulfate, filtered, and concentrated in vacuo. The resulting residue was purified via medium pressure liquid chromatography ($SiO_2$, 100% hexanes to 70% ethyl acetate/hexanes) to provide 4-[6-(2-oxo-1,2-dihydropyridin-1-yl) pyrazolo[1,5-a]pyrimidin-3-yl]-N-(pentan-3-yl)thiophene-2-carboxamide (66.0 mg, 65% yield). 1H NMR (500 MHZ, Chloroform-d) δ 8.78 (d, J=2.4 Hz, 1H), 8.58 (d, J=2.4 Hz, 1H), 8.37 (s, 1H), 8.16 (dd, J=5.5, 2.0 Hz, 1H), 8.07 (d, J=1.5 Hz, 1H), 7.99 (d, J=1.4 Hz, 1H), 7.85-7.77 (m, 1H), 7.16-7.09 (m, 2H), 5.77 (d, J=9.0 Hz, 1H), 4.02 (dtd, J=13.4, 8.1, 5.3 Hz, 1H), 1.78-1.48 (m, 4H), 0.95-0.77 (m, 6H). HRMS (ESI) m/z calculated for $C_{21}H_{22}N_5O_2S$ [M+H], 408.1494; found 408.1491. HPLC purity (AUC): 97.6%

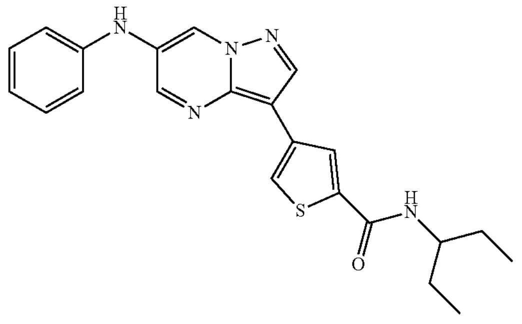 [SMILES: CCC(CC)NC(=O)c1cc(-c2cnn3cc(Nc4ccccc4)cnc23)cs1]

N-(pentan-3-yl)-4-[6-(phenylamino) pyrazolo[1,5-a] pyrimidin-3-yl]thiophene-2-carboxamide A mixture of 4-(6-bromopyrazolo[1,5-a]pyrimidin-3-yl)-N-(pentan-3-yl)thiophene-2-carboxamide (0.025 g, 0.07 mmol), aniline (0.012 g, 0.13 mmol), cesium carbonate (0.069 g, 0.21 mmol), 2,2'-bis(diphenylphosphino)-1,1'-binaphthyl (0.003 g, 0.004 mmol) in toluene (2.0 mL) was sparged for 20 minutes with argon gas (bubbling into the mixture). Palladium acetate (0.001 g, 0.004 mmol) was added, and the mixture heated to 110° C. using an Anton-Parr monowave microwave reactor (12 hours). Upon completion, the reaction was cooled and diluted with ethyl acetate. The mixture was filtered through a small pad of Celite (5 cm) and the pad washed further with additional ethyl acetate (10 mL). The combined filtrates were then washed with water (5×10 mL) and saturated aqueous sodium chloride (2×10 mL). The organic layer was dried with sodium sulfate, filtered, and concentrated in vacuo. The resulting residue was purified via medium pressure liquid chromatography ($SiO_2$, 100% hexanes to 70% ethyl acetate/hexanes) to provide N-(pentan-3-yl)-4-[6-(phenylamino) pyrazolo[1,5-a]pyrimidin-3-yl]thiophene-2-carboxamide (0.018 g, 63% yield). 1H NMR (500 MHZ, Chloroform-d) δ 8.60-8.46 (m, 2H), 8.28 (s, 1H), 8.04 (d, J=1.4 Hz, 1H), 7.97 (d, J=1.4 Hz, 1H), 7.40-7.33 (m, 2H), 7.11-7.00 (m, 3H), 5.76 (d, J=9.1 Hz, 1H), 4.02 (dtd, J=13.5, 8.1, 5.2 Hz, 1H), 1.81-1.64-1.54 (m, 4H), 0.99-0.80 (m, 6H). HRMS (ESI) m/z calculated for $C_{22}H_{24}N_5OS$ [M+H], 406.1702; found 406.1705. HPLC purity (AUC): 96.2%.

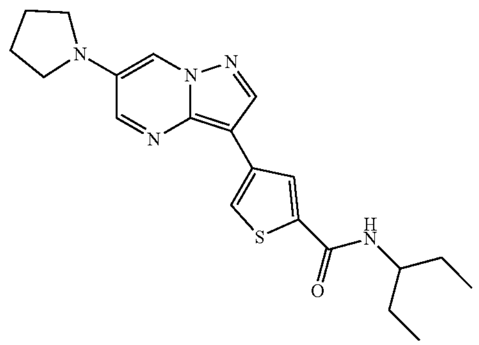 [SMILES: CCC(CC)NC(=O)c1cc(-c2cnn3cc(N4CCCC4)cnc23)cs1]

N-(pentan-3-yl)-4-[6-(pyrrolidin-1-yl) pyrazolo[1,5-a]pyrimidin-3-yl]thiophene-2-carboxamide A mixture of 4-(6-bromopyrazolo[1,5-a]pyrimidin-3-yl)-N-(pentan-3-yl)thiophene-2-carboxamide (0.050 g, 0.013 mmol), pyrrolidine (0.046 g, 0.64 mmol), potassium tert-butoxide (0.073 g, 0.65 mmol), 2,2'-bis(diphenylphosphino)-1,1'-binaphthyl (0.005 mg, 0.007 mmol) in dimethylformamide (4.0 mL) was sparged for 20 minutes with argon gas (bubbling in the mixture). Palladium acetate (0.002 g, 0.007 mmol) was added. The mixture and heated to 120° C. using an Anton-Parr monowave microwave reactor. Upon completion (12 hr), the mixture was cooled and diluted with ethyl acetate. The mixture was filtered through a small pad of Celite (5 cm) and the pad washed with additional ethyl acetate (10 mL). The combined filtrates were washed subsequently with water (5×10 mL) and saturated aqueous sodium chloride (2×10 mL). The organic layer was then dried with sodium sulfate, filtered, and concentrated in vacuo. The resulting residue was purified via reverse phase medium pressure liquid chromatography ($C_{18}$, 100% ammonium formate to 80% methanol/ammonium formate). Fractions that contained the desired product were combined and the volatiles were concentrated in vacuo. The remaining water/residue mixture was extracted with ethyl acetate (4×20 mL) and the combined organic layers were dried with sodium sulfate, filtered, and concentrated in vacuo to provide N-(pentan-3-yl)-4-[6-(phenylamino) pyrazolo[1,5-a]pyrimidin-3-yl]thiophene-2-carboxamide (0.04 g, 73% yield). $^1$H NMR (500 MHz, Chloroform-d) δ 8.26-8.17 (m, 1H), 8.09 (t, J=8.5 Hz, 1H), 7.97 (t, J=7.8 Hz, 1H), 7.70-7.56 (m, 1H), 7.55-7.43 (m, 1H), 5.92 (d, J=6.5 Hz, 1H), 3.98 (m, 5H), 2.16 (m, 4H), 1.75-1.45 (m, 4H), 0.92-0.77 (m, 6H). HRMS (ESI) m/z calculated for $C_{20}H_{26}N_4OS$ [M+H], 384.1858; found 384.1856. HPLC purity (AUC): 93.8%.

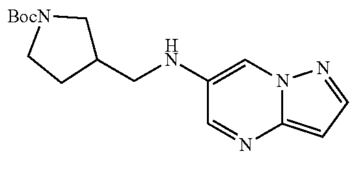 [SMILES: CC(C)(C)OC(=O)N1CCC(CNc2cnc3ccnn3c2)C1]

tert-butyl 3-[(pyrazolo[1,5-a]pyrimidin-6-ylamino) methyl]pyrrolidine-1-carboxylate To a stirred solution of 6-bromopyrazolo[1,5-a]pyrimidine (0.10 g, 0.51 mmol) and tert-butyl 3-(aminomethyl) pyrrolidine-1-carboxylate (0.304 g, 1.52 mmol) in dimethylsulfoxide (3.0 mL), under argon atmosphere, was added diisopropyl ethyl amine (0.50 mL). The mixture was heated to 120° C. in an Anton-Parr monowave microwave reactor and monitored by LC-MS (12 hours).

Upon completion, the reaction was diluted with ethyl acetate and washed subsequently with water (3×10 mL) and saturated aqueous sodium chloride (2×10 mL). The organic layer was dried with sodium sulfate, filtered, and concentrated in vacuo. The resulting residue was purified via medium pressure liquid chromatography ($SiO_2$, 100% hexanes to 70% ethyl acetate/hexanes) to provide tert-butyl 3-[(pyrazolo[1,5-a]pyrimidin-6-ylamino)methyl]pyrrolidine-1-carboxylate (0.133 g, 82% yield). 1H NMR (500 MHZ, Chloroform-d) δ 8.24 (d, J=5.1 Hz, 1H), 8.16 (d, J=6.3 Hz, 1H), 6.52 (s, 1H), 5.94 (d, J=5.1 Hz, 1H), 3.14-2.98 (m, 2H), 2.68-1.80 (m, 4H), 1.53 (s, 9H), 1.29-1.07 (m, 3H).

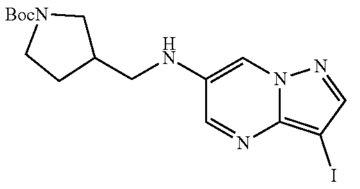 [SMILES: CC(C)(C)OC(=O)N1CCC(CNc2cnc3c(I)cnn3c2)C1]

tert-butyl 3-{[(3-iodopyrazolo[1,5-a]pyrimidin-6-yl) amino]methyl}pyrrolidine-1-carboxylate To a stirred solution of tert-butyl 3-[(pyrazolo[1,5-a] pyrimidin-6-ylamino)methyl]pyrrolidine-1-carboxylate (0.03 g, 0.095 mmol) in dimethylformamide (1.0 mL) under argon atmosphere was added slowly N-iodosuccinimide (0.024 g, 0.11 mmol) portion-wise during 2 minutes. The resulting mixture was stirred at room temperature (4 hours). Upon completion, the mixture was diluted with ethyl acetate and washed subsequently with water (5×2 mL) and saturated aqueous sodium thiosulfate (2×2 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes) to provide tert-butyl 4-(3-iodopyrazolo[1,5-a]pyrimidin-6-yl) piperazine-1-carboxylate (0.04 g, 92% yield). 1H NMR (500 MHZ, Chloroform-d) δ 8.25 (d, J=5.1 Hz, 1H), 8.12 (d, J=6.3 Hz, 1H), 6.50 (s, 1H), 3.12-2.95 (m, 2H), 2.68-1.80 (m, 4H), 1.53 (s, 9H), 1.30-1.23 (m, 3H).

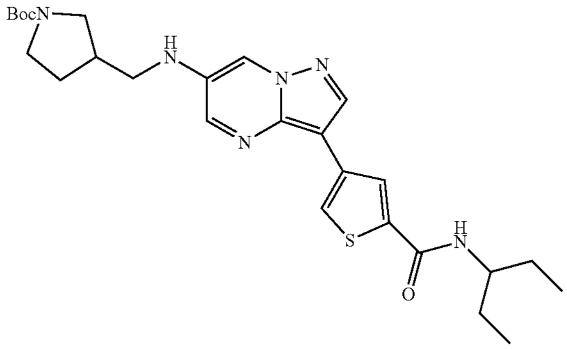 [SMILES: CCC(CC)NC(=O)c1cc(-c2cnn3cc(NCC4CCN(C(=O)OC(C)(C)C)C4)cnc23)cs1]

MSU-43492 (ALE-8-82): tert-butyl 3-{[(3-{5-[(pentan-3-yl) carbamoyl]thiophen-3-yl}pyrazolo[1,5-a]pyrimidin-6-yl)amino]methyl}pyrrolidine-1-carboxylate A mixture of tert-butyl 3-{[(3-iodopyrazolo[1,5-a]pyrimidin-6-yl)amino]methyl}pyrrolidine-1-carboxylate (0.04 g, 0.0.091 mmol), 4-pinacolborane-N-(pentan-3-yl)thiophene-2-carboxamide (0.05 g, 0.14 mmol), potassium phosphate (0.06 g, 0.28 mmol) in dioxane/water (10:1, 2.0 mL) was sparged for 20 minutes with argon gas (bubbling into the mixture). Tetrakis(triphenylphosphine) palladium (0)(0.005 g, 0.05 mmol) was added and the mixture heated to 110° C. using an Anton-Parr monowave microwave reactor (12 hours). Upon completion, the reaction was cooled and diluted with ethyl acetate. The mixture was filtered through a small pad of Celite (5 cm) and pad washed with additional ethyl acetate (5 mL). The combined filtrates were washed subsequently with water (3×5 mL) and saturated aqueous sodium chloride (2×5 mL). The organic layer was dried with sodium sulfate, filtered, and concentrated in vacuo. The resulting residue was purified via reverse phase column chromatography ($C_{18}$, 100% ammonium formate to 40% methanol/ammonium formate). Fractions containing the desired product were combined and the volatiles were concentrated in vacuo. The remaining water residue was extracted with ethyl acetate (4×20 mL) and the combined organic layers dried with sodium sulfate, filtered, and concentrated in vacuo (0.040 g, 79% yield). 1H NMR (500 MHZ, Chloroform-d) δ 8.36 (d, J=5.3 Hz, 1H), 8.28 (s, 1H), 8.19 (s, 1H), 7.90 (d, J=20.1 Hz, 1H), 6.06 (d, J=5.3 Hz, 1H), 4.01 (m, 1H), 3.70-3.50 (m, 4H), 3.30-3.21 (m, 2H), 2.66 (m, 1H), 1.68 (ddd, J=13.2, 7.5, 5.6 Hz, 2H), 1.64-1.50 (m, 2H), 1.43 (m, 2H), 1.47 (s, 9H), 0.98 (t, J=7.4 Hz, 6H). HRMS (ESI) m/z calculated for $C_{26}H_{37}N_6O_3S$ [M+H], 513.2648; found 513.2677. HPLC purity (AUC): 95.0%.

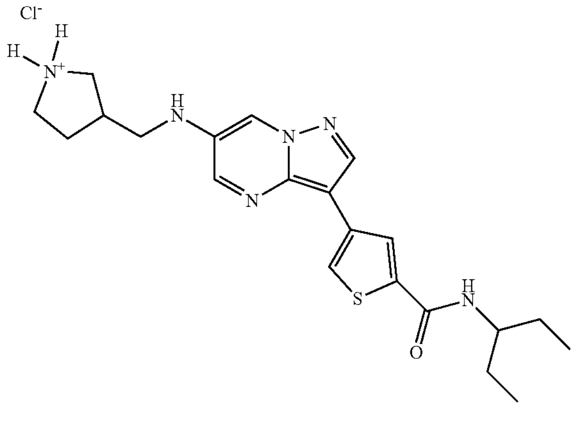 [SMILES: [Cl-] ; CCC(CC)NC(=O)c1cc(-c2cnn3cc(NCC4CC[NH2+]C4)cnc23)cs1]

MSU-43493 (ALE-8-86): N-(pentan-3-yl)-4-{6-[(pyrrolidin-3-ylmethyl)amino]pyrazolo[1,5-a]pyrimidin-3-yl}thiophene-2-carboxamide hydrochloride A mixture of tert-butyl 3-{[(3-{5-[(pentan-3-yl) carbamoyl]thiophen-3-yl}pyrazolo[1,5-a]pyrimidin-6-yl)amino] methyl}pyrrolidine-1-carboxylate (30.0 mg, 0.06 mmol) in methanol (3.0 mL) was treated dropwise with hydrochloric acid (4.0 N in dioxane, 0.15 mL, 0.6 mmol). The mixture was stirred at room temperature, under an argon atmosphere, for 2 hours and concentrated to give the desired HCl salt (0.025 g, 100% yield). 1H NMR (500 MHZ, Methanol-$d_4$) δ 8.39 (s, 1H), 8.32-8.29 (m, 1H), 8.27 (d, J=1.3 Hz, 1H), 8.00 (d, J=1.3 Hz, 1H), 6.32 (d, J=5.3 Hz, 1H), 4.31 (m, 1H), 3.73-3.50 (m, 4H), 3.41-3.35 (m, 2H), 1.60-1.53 (m, 2H), 1.55-1.50 (m, 2H), 1.42 (m, 2H), 1.32 (m, 1H), 1.04-0.94 (m, 6H). HRMS (ESI) m/z calculated for $C_{21}H_{29}N_6OS$ [M+H], 413.2124; found 413.2122. HPLC purity (AUC): 95.0%.

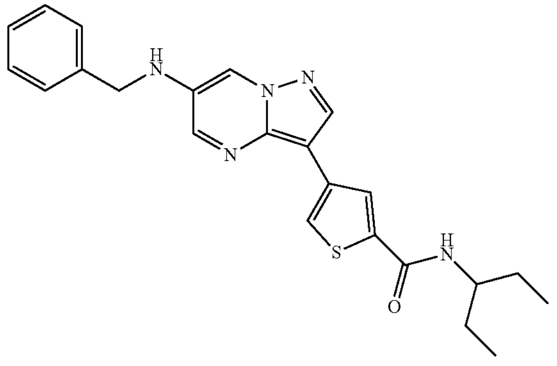 [SMILES: CCC(CC)NC(=O)c1cc(-c2cnn3cc(NCc4ccccc4)cnc23)cs1]

MSU-43456 (ALE-8-48): N-(pentan-3-yl)-4-[6-(benzylamino) pyrazolo[1,5-a]pyrimidin-3-yl]thiophene-2-carboxamide To a stirred solution of 4-(6-bromopyrazolo[1,5-a]pyrimidin-3-yl)-N-(pentan-3-yl)thiophene-2-carboxamide (0.095 g, 0.25 mmol), benzyl amine (0.078 g, 0.73 mmol) in dimethylsulfoxide (3.0 mL), under an argon atmosphere, was added diisopropylethyl amine (0.20 mL). The mixture was heated to 120° C. in an Anton-Parr monowave microwave reactor and monitored by LC-MS (4 hours). Upon completion, the mixture was diluted with ethyl acetate and washed subsequently with water (3×10 mL) and saturated sodium chloride (2×10 mL). The organic layer was dried with sodium sulfate, filtered, and concentrated in vacuo. The resulting residue was purified via reverse phase column chromatography ($C_{18}$, 100% ammonium formate to 40% methanol/ammonium formate). Fractions containing the desired product were combined and the volatiles removed in vacuo. The water residue mixture was extracted with ethyl acetate (4×20 mL) and the combined organic layers dried with sodium sulfate, filtered, and concentrated in vacuo (0.07 g, 68% yield). 1H NMR (500 MHZ, Chloroform-d) δ 8.30 (d, J=5.2 Hz, 1H), 8.25 (s, 1H), 8.06 (d, J=1.3 Hz, 1H), 7.93 (d, J=1.4 Hz, 1H), 7.44-7.32 (m, 5H), 6.81 (t, J=5.9 Hz, 1H), 6.02 (d, J=5.2 Hz, 1H), 5.80 (d, J=9.1 Hz, 1H), 4.65 (d, J=5.8 Hz, 2H), 4.00 (dtd, J=13.6, 8.1, 5.2 Hz, 1H), 1.66 (dtd, J=14.8, 7.4, 5.3 Hz, 2H), 1.51 (dt, J=13.8, 7.5 Hz, 2H), 0.97 (t, J=7.4 Hz, 6H). HRMS (ESI) m/z calculated for $C_{23}H_{25}N_5NaOS$ [M+Na], 442.1678; found 442.1683. HPLC purity (AUC): 97.1%.

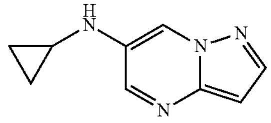 [SMILES: c1cc2ncc(NC3CC3)cn2n1]

(ALE-8-106): N-cyclopropylpyrazolo[1,5-a]pyrimidin-6-amine

To a stirred solution of 6-bromopyrazolo[1,5-a]pyrimidine (0.10 g, 0.51 mmol) and cyclopropyl amine (0.15 g, 2.50 mmol) in DMSO (5.10 mL), under argon atmosphere, was added p-toluene sulfonic acid monohydrate (0.11 g, 0.57 mmol). The mixture was heated to 120° C. in an Anton-Parr monowave microwave reactor and monitored by LC-MS (5 hours). Upon completion, the mixture was cooled, diluted with ethyl acetate, and washed with saturated aqueous sodium bicarbonate (3×100 mL) and water (2×100 mL). The organic layer was dried with sodium sulfate, filtered, and concentrated in vacuo. The resulting residue was purified via medium pressure liquid chromatography ($SiO_2$, 100% hexanes to 70% ethyl acetate/hexanes) to provide N-cyclopropylpyrazolo[1,5-a]pyrimidin-6-amine (0.080 g, 85% yield). 1H NMR (500 MHZ, Chloroform-d) δ 8.27 (dd, J=2.7, 0.9 Hz, 1H), 8.12 (d, J=2.6 Hz, 1H), 7.92 (d, J=2.4 Hz, 1H), 6.59 (dd, J=2.4, 0.9 Hz, 1H), 4.10 (s, 1H), 2.42 (tt, J=6.7, 3.6 Hz, 1H), 0.87-0.75 (m, 2H), 0.66-0.56 (m, 2H).

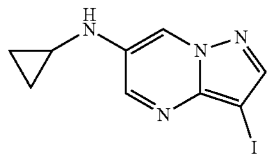 [SMILES: Ic1cnn2cc(NC3CC3)cnc12]

N-cyclopropyl-3-iodopyrazolo[1,5-a]pyrimidin-6-amine

To a stirred solution of N-cyclopropylpyrazolo[1,5-a] pyrimidin-6-amine (0.25 g, 1.44 mmol) in dimethylformamide (15.0 mL), under argon atmosphere, was added slowly N-iodosuccinimide (0.36 g, 1.59 mmol) portion-wise during 5 minutes. Upon completion (4 hours), the mixture was diluted with ethyl acetate and washed with water (5×20 mL) and saturated aqueous sodium thiosulfate (2×20 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes) to provide N-cyclopropyl-3-iodopyrazolo[1,5-a]pyrimidin-6-amine (0.406 g, 94% yield). $^1$H NMR (500 MHZ, Chloroform-d) δ 8.26 (s, 1H), 8.14 (d, J=2.6 Hz, 1H), 7.93 (d, J=2.4 Hz, 1H), 4.11 (s, 1H), 2.42 (m, 1H), 0.83-0.75 (m, 2H), 0.67-0.54 (m, 2H).

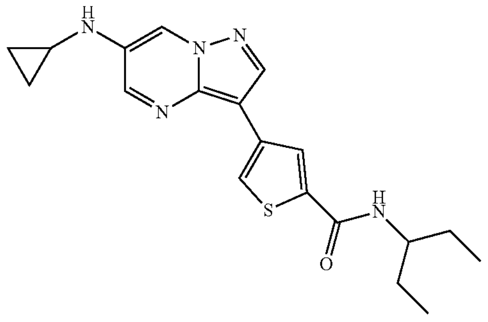 [SMILES: CCC(CC)NC(=O)c1cc(-c2cnn3cc(NC4CC4)cnc23)cs1]

4-[6-(cyclopropylamino) pyrazolo[1,5-a]pyrimidin-3-yl]-N-(pentan-3-yl)thiophene-2-carboxamide A mixture of N-cyclopropyl-3-iodopyrazolo[1,5-a]pyrimidin-6-amine (0.02 g, 0.067 mmol), 4-pinacolborane-N-(pentan-3-yl)thiophene-2-carboxamide (0.044 g, 0.14 mmol) and potassium phosphate (0.043 g, 0.21 mmol) in dioxane/water (10:1, 2.0 mL) sparged for 20 minutes with argon gas (bubbling in the mixture). Tetrakis(triphenylphosphine) palladium (0) (0.008 g, 0.007 mmol) was added and heated to 110° C. using an Anton-Parr monowave microwave reactor (12 hours). Upon completion, the mixture was cooled and diluted with ethyl acetate. The mixture was filtered through a small pad of Celite (5 cm) and the pad washed with additional ethyl acetate (5 mL). The combined filtrates were then washed with water (3×5 mL) and saturated aqueous sodium chloride (2×5 mL). The organic layer was dried with sodium sulfate, filtered, and concentrated in vacuo. The resulting residue was purified via medium pressure liquid chromatography ($SiO_2$, 100% hexanes to 30% ethyl acetate/hexanes) to provide 4-[6-(cyclopropylamino) pyrazolo[1,5-a]pyrimidin-3-yl]-N-(pentan-3-yl)thiophene-2-carboxamide (0.022 g, 86% yield). 1H NMR (500 MHZ, Chloroform-d) δ 8.75 (s, 1H), 8.47 (s, 1H), 8.35 (s, 1H), 7.64 (s, 1H), 6.55 (s, 1H), 3.95 (m, 1H), 2.94 (m, 1H), 1.56-1.42 (m, 4H), 1.07-0.84 (m, 10H). HRMS (ESI) m/z calculated for $C_{19}H_{24}N_5OS$ [M+H], 370.1702; found 370.1708. HPLC purity (AUC): 96.1%.

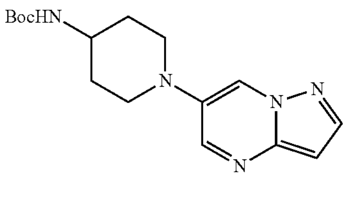 [SMILES: CC(C)(C)OC(=O)NC1CCN(c2cnc3ccnn3c2)CC1]

tert-butyl [1-(pyrazolo[1,5-a]pyrimidin-6-yl) piperidin-4-yl]carbamate

To a stirred solution of 6-bromopyrazolo[1,5-a]pyrimidine (0.582 g, 2.94 mmol) and tert-butyl piperidin-4-ylcarbamate (1.80 g, 8.82 mmol) in dimethylsulfoxide (30.0 mL) was added p-toluene sulfonic acid monohydrate (0.616 g, 3.24 mmol). The mixture was then heated to 120° C. and monitored by LC-MS (16 hours). Upon completion, the mixture was cooled, diluted with ethyl acetate, washed with aqueous sodium bicarbonate (3×100 mL) and water (2×100 mL). The organic layer was dried with sodium sulfate, filtered, and concentrated in vacuo. The resulting residue was then purified via medium pressure liquid chromatography ($SiO_2$, 100% hexanes to 70% ethyl acetate/hexanes) to provide tert-butyl [1-(pyrazolo[1,5-α]pyrimidin-6-yl) piperidin-4-yl]carbamate (0.74 g, 79% yield). 1H NMR (500 MHZ, Chloroform-d) δ 8.45 (d, J=2.7 Hz, 1H), 8.14 (dd, J=2.7, 0.9 Hz, 1H), 7.99 (d, J=2.4 Hz, 1H), 6.61 (dd, J=2.4, 0.9 Hz, 1H), 4.53 (s, 1H), 3.50-3.42 (m, 2H), 2.83 (td, J=11.8, 2.6 Hz, 2H), 2.17-2.08 (m, 2H), 1.64 (dtd, J=12.8, 11.1, 4.0 Hz, 2H), 1.47 (s, 9H).

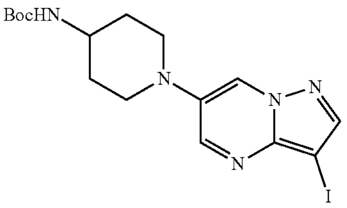 [SMILES: CC(C)(C)OC(=O)NC1CCN(c2cnc3c(I)cnn3c2)CC1]

tert-butyl [1-(3-iodopyrazolo[1,5-a]pyrimidin-6-yl) piperidin-4-yl]carbamate

To a stirred solution of tert-butyl [1-(pyrazolo[1,5-a] pyrimidin-6-yl) piperidin-4-yl]carbamate (0.20 g, 0.64 mmol) in dimethylformamide (7.0 mL), under an argon atmosphere, was added slowly N-iodosuccinimide (0.15 g, 0.67 mmol) portion-wise during 2 minutes. The resulting solution was stirred and upon completion (4 hours), diluted with ethyl acetate and washed with water (5×10 mL) and saturated aqueous sodium thiosulfate (2×10 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes) to provide tert-butyl [1-(3-iodopyrazolo[1,5-a]pyrimidin-6-yl) piperidin-4-yl] carbamate (0.269 g, 96% yield). 1H NMR (500 MHZ, Chloroform-d) δ 8.44 (d, J=2.7 Hz, 1H), 8.13 (s, 1H), 7.98 (d, J=2.4 Hz, 1H), 4.53 (s, 1H), 3.52-3.40 (m, 2H), 2.86 (m, 2H), 2.15-2.08 (m, 2H), 1.63 (m, 2H), 1.48 (s, 9H).

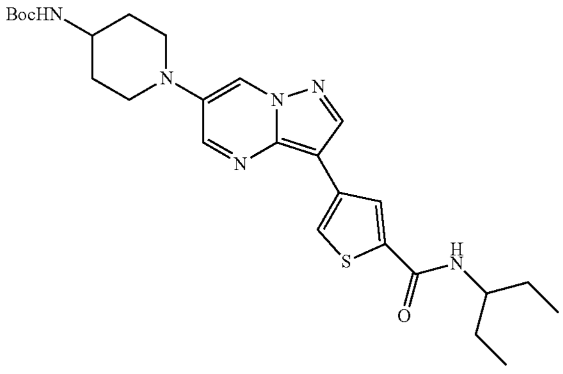 [SMILES: CCC(CC)NC(=O)c1cc(-c2cnn3cc(N4CCC(NC(=O)OC(C)(C)C)CC4)cnc23)cs1]

tert-butyl N-{1-[3-(5-{1-[(pentan-3-yl)amino] ethenyl}thiophen-3-yl) pyrazolo[1,5-a]pyrimidin-6-yl]piperidin-4-yl}carbamate A mixture of tert-butyl [1-(3-iodopyrazolo[1,5-a]pyrimidin-6-yl) piperidin-4-yl]carbamate (0.30 g, 0.68 mmol), 4-pinacolborane-N-(pentan-3-yl)thiophene-2-carboxamide (0.241 g, 0.75 mmol), and potassium phosphate (0.435 g, 2.04 mmol) in dioxane/water (10:1, 15.0 mL) was sparged for 20 minutes with argon gas (bubbling into the mixture).

Tetrakis(triphenylphosphine) palladium (0)(0.008 g, 0.07 mmol) was then added and the mixture heated to 110° C. using an Anton-Parr monowave microwave reactor (12 hours). Upon completion, the mixture was cooled and diluted with ethyl acetate. The mixture was filtered through a small pad of Celite (5 cm) and the pad washed with additional ethyl acetate (15 mL). The combined filtrates were then washed with water (3×15 mL) and saturated aqueous sodium chloride (2×15 mL). The organic layer was then dried with sodium sulfate, filtered, and concentrated in vacuo. The resulting residue was purified via medium pressure liquid chromatography ($SiO_2$, 100% hexanes to 70% ethyl acetate/hexanes) to give tert-butyl N-{1-[3-(5-{1-[(pentan-3-yl)amino]ethenyl}thiophen-3-yl) pyrazolo[1,5-a]pyrimidin-6-yl]piperidin-4-yl}carbamate (0.31 g, 88% yield). 1H NMR (500 MHZ, Chloroform-d) δ 8.53 (d, J=2.6 Hz, 1H), 8.23 (s, 1H), 8.16 (s, 1H), 8.02 (d, J=1.3 Hz, 1H), 7.94 (d, J=1.4 Hz, 1H), 5.72 (d, J=9.0 Hz, 1H), 4.53 (m, 2H), 4.01 (m, 2H), 3.66 (s, 4H), 3.54-3.45 (m, 3H), 2.88 (m, 4H), 2.20-2.12 (m, 3H), 1.75-1.52 (m, 6H), 0.99 (td, J=7.4, 4.3 Hz, 6H). HRMS (ESI) m/z calculated for $C_{26}H_{36}N_6NaO_3S$ [M+Na], 535.2467; found 535.2465. HPLC purity (AUC): 97.6%.

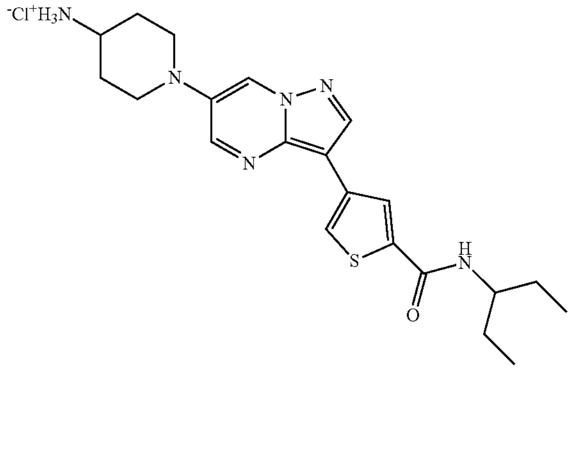

4-[6-(4-aminopiperidin-1-yl) pyrazolo[1,5-a]pyrimidin-3-yl]-N-(pentan-3-yl)thiophene-2-carboxamide hydrochloride A mixture of tert-butyl N-{1-[3-(5-{1-[(pentan-3-yl) amino]ethenyl}thiophen-3-yl) pyrazolo[1,5-a]pyrimidin-6-yl]piperidin-4-yl}carbamate (0.014 mg, 0.03 mmol) in methanol (2.0 mL) was treated dropwise with hydrochloric acid (4.0 N in dioxane, 0.07 mL, 0.30 mmol). The mixture was stirred at room temperature, under an argon atmosphere, for 2 hours then concentrated in vacuo to give the desired HCl salt (0.013 g, 100% yield). 1H NMR (500 MHz, Methanol-$d_4$) δ 8.70 (d, J=2.6 Hz, 1H), 8.43 (d, J=11.3 Hz, 1H), 8.34 (s, 1H), 8.31 (d, J=1.4 Hz, 1H), 8.10 (d, J=1.4 Hz, 1H), 3.87 (tq, J=8.1, 4.1, 3.3 Hz, 1H), 3.78-3.71 (m, 3H), 3.70-3.62 (m, 2H), 3.58 (dd, J=5.5, 4.2 Hz, 1H), 2.96-2.84 (m, 2H), 2.18 (d, J=12.3 Hz, 2H), 1.87 (m, 2H), 1.76-1.65 (m, 2H), 1.64-1.49 (m, 2H), 0.97 (td, J=7.4, 5.4 Hz, 6H). HRMS (ESI) m/z calculated for $C_{21}H_{29}N_6OS$ [M+H], 413.2124; found 413.2124. HPLC purity (AUC): 96.5%.

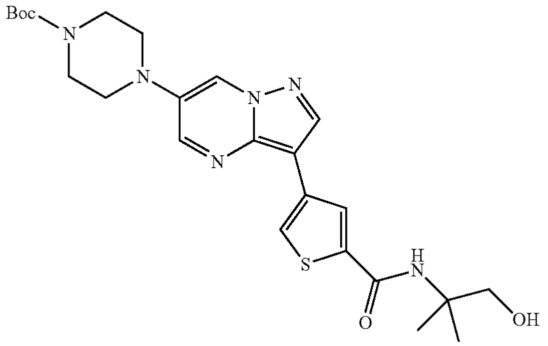 [SMILES: CC(C)(CO)NC(=O)c1cc(-c2cnn3cc(N4CCN(C(=O)OC(C)(C)C)CC4)cnc23)cs1]

tert-butyl 4-(3-{5-[(1-hydroxy-2-methylpropan-2-yl) carbamoyl]thiophen-3-yl}pyrazolo[1,5-a]pyrimidin-6-yl) piperazine-1-carboxylate A mixture of tert-butyl 4-(3-iodopyrazolo[1,5-a]pyrimidin-6-yl) piperazine-1-carboxylate (0.032 g, 0.080 mmol), 4-pinacolborane-N-(1-hydroxy-2-methylpropan-2-yl)thiophene-2-carboxamide (0.026 g, 0.081 mmol), and potassium phosphate (0.052 g, 0.24 mmol) in dioxane/water (10:1, 3.0 mL), was sparged for 20 minutes with argon gas (bubbling into the mixture). Tetrakis(triphenylphosphine) palladium (0)(0.001 g, 0.008 mmol) was added. The mixture was then heated to 110° C. using an Anton-Parr monowave microwave reactor (12 hours). Upon completion, the mixture was cooled and diluted with ethyl acetate. The mixture was filtered through a small pad of Celite (5 cm) and the pad washed with addtional ethyl acetate (10 mL). The combined filtrates were then washed with water (3×10 mL) and saturated aqueous sodium chloride (2×10 mL). The organic layer was dried with sodium sulfate, filtered, and concentrated in vacuo. The resulting residue was purified via reverse phase column chromatography ($C_{18}$, 100% ammonium formate to 40% methanol/ammonium formate). Fractions containing the desired product were combined and the volatiles concentrated in vacuo. The water/residue mixture was extracted with ethyl acetate (4×20 mL) and the combined organic layers dried with sodium sulfate, filtered, and concentrated in vacuo (0.032 g, 79% yield). 1H NMR (500 MHZ, Chloroform-d) δ 8.56 (d, J=2.6 Hz, 1H), 8.23 (d, J=23.1 Hz, 2H), 8.02 (t, J=1.6 Hz, 1H), 7.99-7.82 (m, 1H), 7.52-7.39 (m, 1H), 6.16 (s, 1H), 3.73 (s, 2H), 3.69 (m, 4H), 3.12 (m, 4H), 1.51 (s, 9H), 1.45 (s, 6H). HRMS (ESI) m/z calculated for $C_{24}H_{33}N_{604}S$ [M+H], 501.2284; found 501.2281. HPLC purity (AUC): 98.2%.

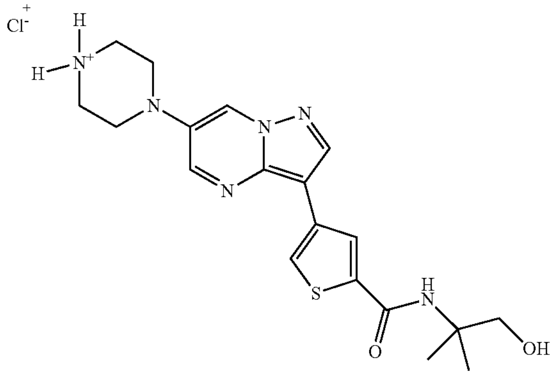 [SMILES: [Cl-] ; CC(C)(CO)NC(=O)c1cc(-c2cnn3cc(N4CC[NH2+]CC4)cnc23)cs1]

N-(1-hydroxy-2-methylpropan-2-yl)-4-[6-(piperazin-1-yl) pyrazolo[1,5-a]pyrimidin-3-yl]thiophene-2-carboxamide hydrochloride A mixture of tert-butyl 4-(3-{5-[(1-hydroxy-2-methylpropan-2-yl) carbamoyl]thiophen-3-yl}pyrazolo[1,5-a]pyrimidin-6-yl) piperazine-1-carboxylate (0.030 mg, 0.060 mmol) in methanol (2.0 mL) was treated dropwise with hydrochloric acid (4.0 N in dioxane, 0.15 mL, 0.60 mmol) and stirred at room temperature, under an argon atmosphere, for 2 hours, then concentrated to give the desired HCl salt (0.026 g, 100% yield). 1H NMR (500 MHZ, Methanol-$d_4$) δ 8.74 (d, J=2.6 Hz, 1H), 8.54 (dd, J=6.6, 2.0 Hz, 2H), 8.45 (s, 1H), 8.32 (d, J=1.5 Hz, 1H), 7.66 (ddt, J=8.6, 5.4, 1.4 Hz, 1H), 7.57 (ddd, J=10.7, 6.5, 3.2 Hz, 1H), 3.54 (s, 2H), 3.50-3.46 (m, 8H), 1.54-1.45 (m, 6H). HRMS (ESI) m/z calculated for $C_{19}H_{25}N_6O_2S$ [M+H], 401.1760; found 401.1756. HPLC purity (AUC): 95.3%.

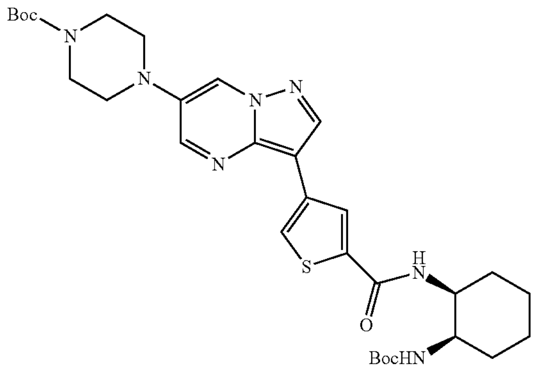 [SMILES: CC(C)(C)OC(=O)N[C@@H]1CCCC[C@@H]1NC(=O)c1cc(-c2cnn3cc(N4CCN(C(=O)OC(C)(C)C)CC4)cnc23)cs1]

tert-butyl 4-[3-(5-{[(1S,2R)-2-{[(tert-butoxy) carbonyl]amino}cyclohexyl]carbamoyl}thiophen-3-yl) pyrazolo[1,5-a]pyrimidin-6-yl]piperazine-1-carboxylate A mixture of tert-butyl 4-(3-iodopyrazolo[1,5-a]pyrimidin-6-yl) piperazine-1-carboxylate (0.085 g, 0.20 mmol), 4-pinacolborane-tert-butyl {(1S,2R)-2-[(thiophen ylcarbonyl)amino]cyclohexyl}carbamate (0.099 g, 0.22 mmol), and potassium phosphate (0.128 g, 0.60 mmol) in dioxane/water (10:1, 4.0 mL) was sparged for 20 minutes with argon gas (bubbling into the mixture). Tetrakis(triphenylphosphine) palladium (0)(0.024 g, 0.020 mmol) was added and heated to 110° C. using an Anton-Parr monowave microwave reactor. Upon completion, the mixture was cooled and diluted with ethyl acetate. The mixture was filtered through a small pad of Celite (5 cm) and the pad washed with additional ethyl acetate (10 mL). The combined filtrates were washed subsequently with water (3×10 mL) and saturated aqueous sodium chloride (2×10 mL). The organic layer was then dried with sodium sulfate, filtered, and concentrated in vacuo. The resulting residue was purified via medium pressure liquid chromatography ($SiO_2$, 100% hexanes to 70% ethyl acetate/hexanes) to provide tert-butyl 4-[3-(5-{[(1S,2R)-2-{[(tertbutoxy) carbonyl] amino}cyclohexyl]carbamoyl}thiophen-3-yl) pyrazolo[1,5-a]pyrimidin-6-yl]piperazine-1-carboxylate (0.102 g, 81% yield). 1H NMR (500 MHz, Chloroform-d) δ 8.50 (dd, J=16.7, 2.6 Hz, 1H), 8.20 (s, 1H), 8.13 (d, J=2.6 Hz, 1H), 8.03-8.00 (m, 1H), 7.98 (d, J=1.4 Hz, 1H), 4.96 (m, 1H), 4.02 (m, 1H), 3.66 (q, J=6.2, 5.7 Hz, 4H), 3.09 (t, J=5.1 Hz, 4H), 1.78-1.70 (m, 2H), 1.66-1.58 (m, 2H), 1.51 (d, J=6.7 Hz, 18H), 1.42-1.33 (m, 2H), 1.25 (m, 2H). HRMS (ESI) m/z calculated for $C_{31}H_{43}N_7NaO_5S$ [M+Na], 648.2944; found 648.2965. HPLC purity (AUC): 96.1%.

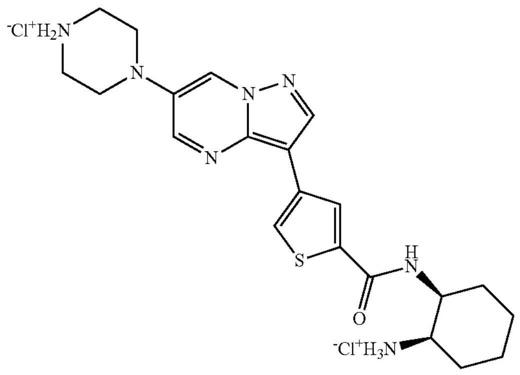

N-[(1S,2R)-2-aminocyclohexyl]-4-[6-(piperazin-1-yl) pyrazolo[1,5-a]pyrimidin-3-yl]thiophene-2-carboxamide dihyrochloride A mixture of tert-butyl 4-[3-(5-{[(1S,2R)-2-{[(tert-butoxy) carbonyl]amino}cyclohexyl]carbamoyl}thiophen-3-yl) pyrazolo[1,5-a]pyrimidin-6-yl]piperazine-1-carboxylate (0.020 g, 0.032 mmol) in methanol (2.0 mL) was treated dropwise with hydrochloric acid (4.0 N in dioxane, 0.080 mL, 0.32 mmol). The mixture was stirred at room temperature, under an argon atmosphere, for 2 hours, then concentrated in vacuo to give the desired HCl salt (0.016 g, 100% yield). 1H NMR (500 MHZ, Methanol-$d_4$) δ 8.73 (d, J=2.6 Hz, 1H), 8.55-8.50 (m, 1H), 8.50 (dd, J=12.9, 1.5 Hz, 1H), 8.42 (s, 1H), 8.20 (d, J=1.4 Hz, 1H), 4.50-4.45 (m, 1H), 3.54 (s, 1H), 3.48 (s, 8H), 3.47-3.41 (m, 2H), 2.02-1.69 (m, 4H), 1.71-1.43 (m, 1H), 1.20 (s, 1H). HRMS (ESI) m/z calculated for $C_{21}H_{28}N_7OS$ [M+H], 426.2076; found 426.2081. HPLC purity (AUC): 95.6%.

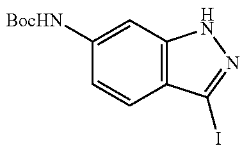 [SMILES: CC(C)(C)OC(=O)Nc1ccc2c(I)n[nH]c2c1]

tert-butyl (3-iodo-1H-indazol-6-yl) carbamate

To a stirred solution of tert-butyl 1H-indazol-6-ylcarbamate (0.32 g, 1.38 mmol) in dimethylformamide (14.0 mL) and under argon atmosphere was added slowly N-iodosuccinimide (0.34 g, 1.51 mmol) portion-wise during 5 minutes. The resulting mixture was stirred at room temperature (4 hours). Upon completion, the reaction was diluted with ethyl acetate and washed subsequently with water (5×20 mL) and saturated aqueous sodium thiosulfate (2×20 mL). The organic layer was dried with sodium sulfate, filtered, and concentrated in vacuo. The resulting residue was purified via medium pressure liquid chromatography ($SiO_2$, 100% hexanes to 10% ethyl acetate/hexanes) to provide tert-butyl (3-iodo-1H-indazol-6-yl) carbamate (0.445 g, 90% yield). 1H NMR (500 MHZ, DMSO-$d_6$) δ 13.21 (s, 1H), 9.61 (s, 1H), 7.83 (s, 1H), 7.25 (d, J=8.7 Hz, 1H), 7.14 (dd, J=8.8, 1.8 Hz, 1H), 2.51-2.46 (m, 1H), 1.48 (s, 9H).

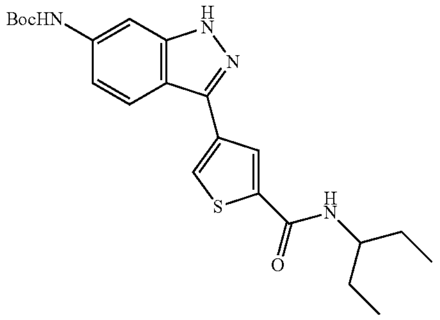 [SMILES: CCC(CC)NC(=O)c1cc(-c2n[nH]c3cc(NC(=O)OC(C)(C)C)ccc23)cs1]

tert-butyl N-(3-{5-[(pentan-3-yl) carbamoyl]thiophen-3-yl}-1H-indazol-6-yl) carbamate A mixture of tert-butyl (3-iodo-1H-indazol-6-yl) carbamate (0.22 g, 0.62 mmol), 4-pinacolborane-N-(pentan-3-yl) thiophene-2-carboxamide (0.22 g, 0.68 mmol) and potassium phosphate (0.396 g, 1.86 mmol) in dioxane/water (10:1, 10.0 mL), was sparged for 20 minutes with argon gas (bubbling into the mixture). Tetrakis(triphenylphosphine) palladium (0)(0.072 g, 0.062 mmol) was added and the mixture heated to 110° C. using an Anton-Parr monowave microwave reactor (12 hours). Upon completion, the mixture was cooled to room temperature and diluted with ethyl acetate. The mixture was filtered through a small pad of Celite (5 cm) and the pad then washed with addtional ethyl acetate (10 mL). The combined filtrates were washed with water (3×10 mL) and saturated aqueous sodium chloride (2×10 mL). The organic layer was dried with sodium sulfate, filtered, and concentrated in vacuo. The resulting residue was purified via reverse phase column chromatography ($C_{18}$, 100% ammonium formate to 40% methanol/ammonium formate). Fractions containing the desired product were combined and the volatiles removed in vacuo. The water/residue mixture was extracted with ethyl acetate (4×20 mL) and the organic layer dried with sodium sulfate, filtered, and concentrated in vacuo to provide the title compound (0.215 g, 81% yield). 1H NMR (500 MHZ, Chloroform-d) δ 8.25 (s, 1H), 8.00 (d, J=1.3 Hz, 1H), 7.93 (s, 1H), 7.85 (d, J=8.8 Hz, 1H), 7.17-7.12 (m, 1H), 7.02 (s, 1H), 6.12 (d, J=9.0 Hz, 1H), 4.07-3.92 (m, 1H), 1.76-1.64 (m, 2H), 1.62-1.48 (m, 11H), 1.06-0.90 (m, 6H). HRMS (ESI) m/z calculated for $C_{22}H_{29}N_4O_3S$ [M+H], 429.1960; found 429.1962. HPLC purity (AUC): 98.0%.

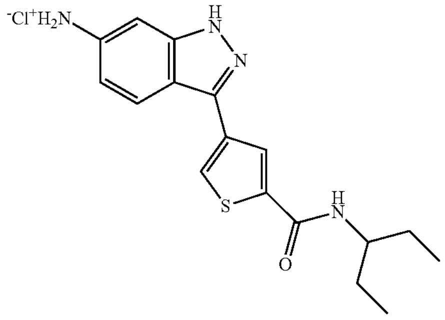

4-(6-amino-1H-indazol-3-yl)-N-(pentan-3-yl)thiophene-2-carboxamide

A mixture of tert-butyl N-(3-{5-[(pentan-3-yl) carbamoyl]thiophen-3-yl}-1H-indazol-6-yl) carbamate (0.015 g, 0.035 mmol) in methanol (2.0 mL) was treated dropwise with hydrochloric acid (4.0 N in dioxane, 0.090 mL, 0.35 mmol). The mixture was stirred at room temperature, under an argon atmosphere, for 2 hours and concentrated to give the desired HCl salt (0.013 g, 100% yield). 1H NMR (500 MHZ, Methanol-$d_4$) δ 8.34 (d, J=1.4 Hz, 1H), 8.31 (d, J=8.6 Hz, 1H), 8.20 (d, J=1.4 Hz, 1H), 7.66-7.62 (m, 1H), 7.25 (dd, J=8.7, 1.8 Hz, 1H), 3.88 (tt, J=8.9, 4.9 Hz, 1H), 1.74-1.64 (m, 2H), 1.63-1.50 (m, 2H), 0.98 (t, J=7.4 Hz, 6H). HRMS (ESI) m/z calculated for $C_{17}H_{21}N_4OS$ [M+H], 329.1436; found 329.1431. HPLC purity (AUC): 95.6%.

TABLE 1

| Exemplary Compounds | | | | | | |
|---|---|---|---|---|---|---|
| Structure Molecular Weight | NMR and HRMS | cLogP | Kinetic Solubility (μM) | ULK1 $IC_{50}$ | ULK2 $IC_{50}$ | Cell $EC_{50}$ |
| 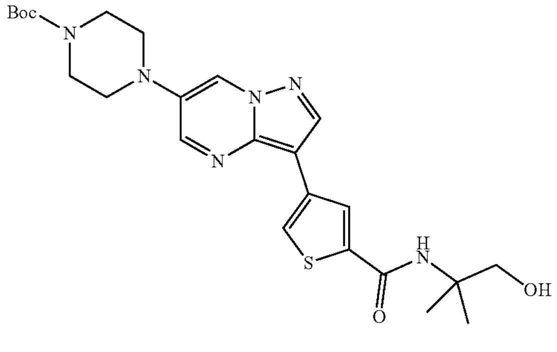 [SMILES: CC(C)(CO)NC(=O)c1cc(-c2cnn3cc(N4CCN(C(=O)OC(C)(C)C)CC4)cnc23)cs1] MW 500.62 | $^1H$ NMR (500 MHz, Chloroform-d) δ 8.56 (d, J = 2.6 Hz, 1H), 8.23 (d, J = 23.1 Hz, 2H), 8.02 (t, J = 1.6 Hz, 1H), 7.99-7.82 (m, 1H), 7.52-7.39 (m, 1H), 6.16 (s, 1H), 3.73 (s, 2H), 3.69 (m, 4H), 3.12 (m, 4H), 1.51 (s, 9H), 1.45 (s, 6H). HRMS (ESI) m/z calculated for $C_{24}H_{33}N_6O_4S$ [M + H], 501.2284; found 501.2281. HPLC purity (AUC): 98.2%. | 3.02 | — | A | C | — |
| 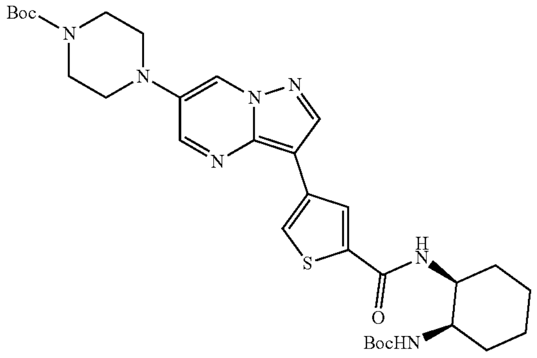 [SMILES: CC(C)(C)OC(=O)N[C@@H]1CCCC[C@@H]1NC(=O)c1cc(-c2cnn3cc(N4CCN(C(=O)OC(C)(C)C)CC4)cnc23)cs1] MW 625.79 | $^1H$ NMR (500 MHz, Chloroform-d) δ 8.50 (dd, J = 16.7, 2.6 Hz, 1H), 8.20 (s, 1H), 8.13 (d, J = 2.6 Hz, 1H), 8.03-8.00 (m, 1H), 7.98 (d, J = 1.4 Hz, 1H), 4.96 (m, 1H), 4.02 (m, 1H), 3.66 (q, J = 6.2, 5.7 Hz, 4H), 3.09 (t, J = 5.1 Hz, 4H), 1.78-1.70 (m, 2H), 1.66-1.58 (m, 2H), 1.51 (d, J = 6.7 Hz, 18H), 1.42-1.33 (m, 2H), 1.25 (m, 2H). HRMS (ESI) m/z calculated for $C_{31}H_{43}N_7NaO_5S$ [M + Na], 648.2944; found 648.2965. HPLC purity (AUC): 96.1%. | 5.59 | — | C | D | — |
| 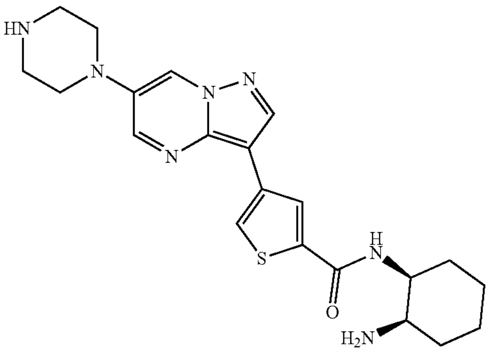 [SMILES: N[C@@H]1CCCC[C@@H]1NC(=O)c1cc(-c2cnn3cc(N4CCNCC4)cnc23)cs1] | $^1H$ NMR (500 MHz, Methanol-$d_4$) δ 8.73 (d, J = 2.6 Hz, 1H), 8.55-8.50 (m, 1H), 8.50 (dd, J = 12.9, 1.5 Hz, 1H), 8.42 (s, 1H), 8.20 (d, J = 1.4 Hz, 1H), 4.50-4.45 (m, 1H), 3.54 (s, 1H), 3.48 (s, 8H), 3.47-3.41 (m, 2H), 2.02-1.69 (m, 4H), 1.71-1.43 (m, 1H), 1.20 (s, 1H). | 1.80 | >300 | A | A | A |

TABLE 1-continued

Exemplary Compounds

| Structure Molecular Weight | NMR and HRMS | cLogP | Kinetic Solubility (μM) | ULK1 $IC_{50}$ | ULK2 $IC_{50}$ | Cell $EC_{50}$ |
|---|---|---|---|---|---|---|
| MW (di-HCl salt) 498.48 | HRMS (ESI) m/z calculated for $C_{21}H_{28}N_7OS$ [M + H], 426.2076; found 426.2081. HPLC purity (AUC): 95.6%. | | | | | |
| 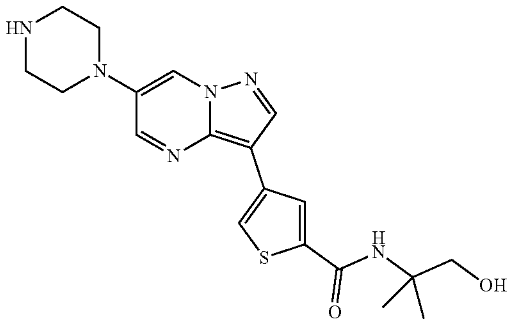 [SMILES: CC(C)(CO)NC(=O)c1cc(-c2cnn3cc(N4CCNCC4)cnc23)cs1] MW (HCl salt) 436.96 | $^1$H NMR (500 MHz, Methanol-$d_4$) δ 8.74 (d, J = 2.6 Hz, 1H), 8.54 (dd, J = 6.6, 2.0 Hz, 2H), 8.45 (s, 1H), 8.32 (d, J = 1.5 Hz, 1H), 7.66 (ddt, J = 8.6, 5.4, 1.4 Hz, 1H), 7.57 (ddd, J = 10.7, 6.5, 3.2 Hz, 1H), 3.54 (s, 2H), 3.50-3.46 (m, 8H), 1.54-1.45 (m, 6H). HRMS (ESI) m/z calculated for $C_{19}H_{25}N_6O_2S$ [M + H], 401.1760; found 401.1756. HPLC purity (AUC): 95.3%. | 1.03 | — | C | D | — |
| 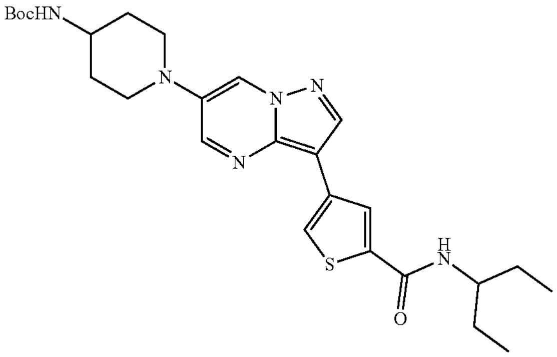 [SMILES: CCC(CC)NC(=O)c1cc(-c2cnn3cc(N4CCC(NC(=O)OC(C)(C)C)CC4)cnc23)cs1] MW 512.68 | $^1$H NMR (500 MHz, Chloroform-d) δ 8.53 (d, J = 2.6 Hz, 1H), 8.23 (s, 1H), 8.16 (s, 1H), 8.02 (d, J = 1.3 Hz, 1H), 7.94 (d, J = 1.4 Hz, 1H), 5.72 (d, J = 9.0 Hz, 1H), 4.53 (m, 2H), 4.01 (m, 2H), 3.66 (s, 4H), 3.54-3.45 (m, 3H), 2.88 (m, 4H), 2.20-2.12 (m, 3H), 1.75-1.52 (m, 6H), 0.99 (td, J = 7.4, 4.3 Hz, 6H). HRMS (ESI) m/z calculated for $C_{26}H_{36}N_6NaO_3S$ [M + Na], 535.2467; found 535.2465. HPLC purity (AUC): 97.6%. | 3.93 | — | B | — | E |

TABLE 1-continued

| Exemplary Compounds | | | | | | |
|---|---|---|---|---|---|---|
| Structure<br>Molecular Weight | NMR and HRMS | cLogP | Kinetic Solubility (μM) | ULK1 $IC_{50}$ | ULK2 $IC_{50}$ | Cell $EC_{50}$ |
| 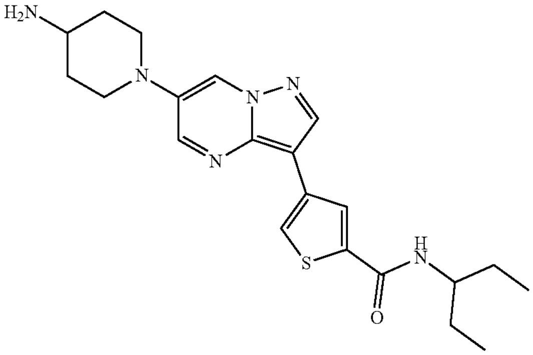<br>MW (HCl salt) 449.02 | $^1$H NMR (500 MHz, Methanol-$d_4$) δ 8.70 (d, J = 2.6 Hz, 1H), 8.43 (d, J = 11.3 Hz, 1H), 8.34 (s, 1H), 8.31 (d, J = 1.4 Hz, 1H), 8.10 (d, J = 1.4 Hz, 1H), 3.87 (tq, J = 8.1, 4.1, 3.3 Hz, 1H), 3.78-3.71 (m, 3H), 3.70-3.62 (m, 2H), 3.58 (dd, J = 5.5, 4.2 Hz, 1H), 2.96-2.84 (m, 2H), 2.18 (d, J = 12.3 Hz, 2H), 1.87 (m, 2H), 1.76-1.65 (m, 2H), 1.64-1.49 (m, 2H), 0.97 (td, J = 7.4, 5.4 Hz, 6H). HRMS (ESI) m/z calculated for $C_{21}H_{29}N_6OS$ [M + H], 413.2124; found 413.2124. HPLC purity (AUC): 96.5%. | 2.19 | 203 | A | B | C |
| 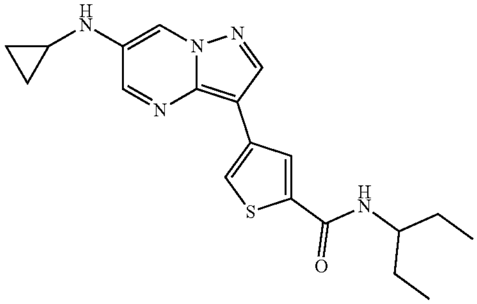 [SMILES: CCC(CC)NC(=O)c1cc(-c2cnn3cc(NC4CC4)cnc23)cs1]<br>MW 369.49 | $^1$H NMR (500 MHz, Chloroform-d) δ 8.75 (s, 1H), 8.47 (s, 1H), 8.35 (s, 1H), 7.64 (s, 1H), 6.55 (s, 1H), 3.95 (m, 1H), 2.94 (m, 1H), 1.56-1.42 (m, 4H), 1.07-0.84 (m, 10H). HRMS (ESI) m/z calculated for $C_{19}H_{24}N_5OS$ [M + H], 370.1702; found 370.1708. HPLC purity (AUC): 96.1%. | 3.91 | — | C | — | — |
| 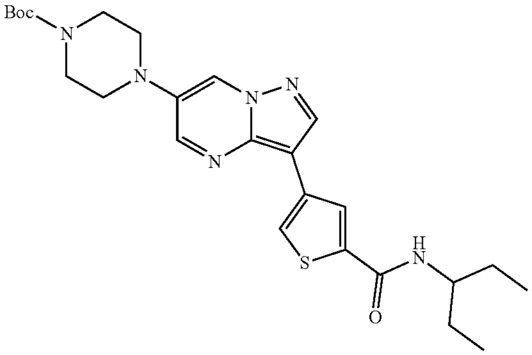 [SMILES: CCC(CC)NC(=O)c1cc(-c2cnn3cc(N4CCN(C(=O)OC(C)(C)C)CC4)cnc23)cs1]<br>MW 498.65 | $^1$H NMR (500 MHz, Chloroform-d) δ 8.53 (d, J = 2.6 Hz, 1H), 8.25 (s, 1H), 8.13 (d, J = 2.6 Hz, 1H), 8.02 (d, J = 1.4 Hz, 1H), 7.95 (d, J = 1.4 Hz, 1H), 5.74 (d, J = 9.1 Hz, 1H), 4.06-3.98 (m, 1H), 3.66 (q, J = 8.1, 6.6 Hz, 4H), 3.09 (d, J = 5.4 Hz, 4H), 1.75-1.61 (m, 2H), 1.55-1.52 (m, 2H), 1.51 (s, 9H), 0.99 (t, J = 7.4 Hz, 6H). HRMS | 4.77 | — | A | — | E |

TABLE 1-continued

| Exemplary Compounds | | | | | | |
|---|---|---|---|---|---|---|
| Structure<br>Molecular Weight | NMR and HRMS | cLogP | Kinetic Solubility (μM) | ULK1 $IC_{50}$ | ULK2 $IC_{50}$ | Cell $EC_{50}$ |
| | (ESI) m/z calculated for $C_{25}H_{34}N_6NaO_3S$ [M + Na], 521.2311; found 521.2311. HPLC purity (AUC): 98.6%. | | | | | |
| 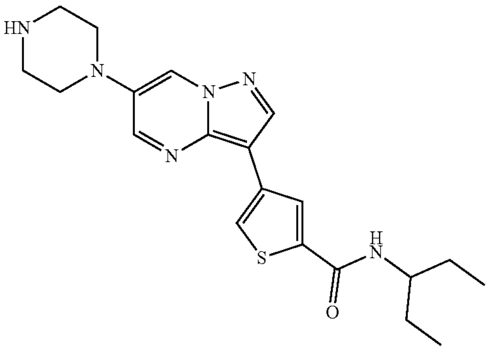 [SMILES: CCC(CC)NC(=O)c1cc(-c2cnn3cc(N4CCNCC4)cnc23)cs1]<br>MW 434.99 (HCl salt) | $^1$H NMR (500 MHz, Methanol-$d_4$) δ 8.72 (d, J = 2.6 Hz, 1H), 8.52 (d, J = 2.6 Hz, 1H), 8.38 (s, 1H), 8.32 (d, J = 1.4 Hz, 1H), 8.12 (d, J = 1.3 Hz, 1H), 3.88 (tt, J = 8.7, 5.0 Hz, 1H), 3.78-3.71 (m, 2H), 3.69-3.67 (m, 2H), 3.59 (m, 2H), 3.46 (m, 2H), 1.77-1.58 (m, 2H), 1.63-1.51 (m, 2H), 0.98 (t, J = 7.4 Hz, 6H). HRMS (ESI) m/z calculated for $C_{20}H_{27}N_6OS$ [M + H], 399.1967; found 399.1963. HPLC purity (AUC): 97.2%. | 2.78 | >300 | B | C | D |
| 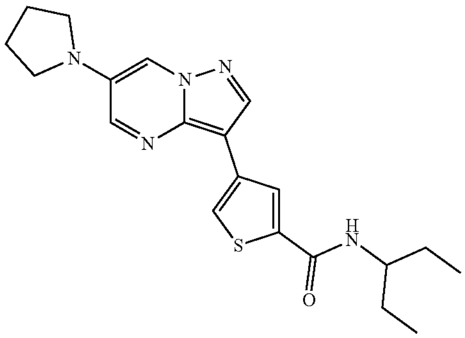 [SMILES: CCC(CC)NC(=O)c1cc(-c2cnn3cc(N4CCCC4)cnc23)cs1]<br>MW 383.51 | $^1$H NMR (500 MHz, Chloroform-d) δ 8.26-8.17 (m, 1H), 8.09 (t, J = 8.5 Hz, 1H), 7.97 (t, J = 7.8 Hz, 1H), 7.70-7.56 (m, 1H), 7.55-7.43 (m, 1H), 5.92 (d, J = 6.5 Hz, 1H), 3.98 (m, 5H), 2.16 (m, 4H), 1.75-1.45 (m, 4H), 0.92-0.77 (m, 6H). HRMS (ESI) m/z calculated for $C_{20}H_{26}N_4OS$ [M + H], 384.1858; found 384.1856. HPLC purity (AUC): 93.8%. | 3.62 | — | D | — | — |

TABLE 1-continued

| Exemplary Compounds | | | | | | |
|---|---|---|---|---|---|---|
| Structure Molecular Weight | NMR and HRMS | cLogP | Kinetic Solubility (μM) | ULK1 $IC_{50}$ | ULK2 $IC_{50}$ | Cell $EC_{50}$ |
| 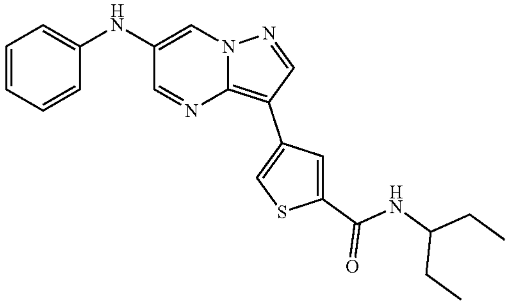 [SMILES: CCC(CC)NC(=O)c1cc(-c2cnn3cc(Nc4ccccc4)cnc23)cs1] MW 405.5200 | $^1$H NMR (500 MHz, Chloroform-d) δ 8.60-8.46 (m, 2H), 8.28 (s, 1H), 8.04 (d, J = 1.4 Hz, 1H), 7.97 (d, J = 1.4 Hz, 1H), 7.40-7.33 (m, 2H), 7.11-7.00 (m, 3H), 5.76 (d, J = 9.1 Hz, 1H), 4.02 (dtd, J = 13.5, 8.1, 5.2 Hz, 1H), 1.81-1.64-1.54 (m, 4H), 0.99-0.80 (m, 6H). HRMS (ESI) m/z calculated for $C_{22}H_{24}N_5OS$ [M + H], 406.1702; found 406.1705. HPLC purity (AUC): 96.2%. | 5.16 | — | A | A | C |
| 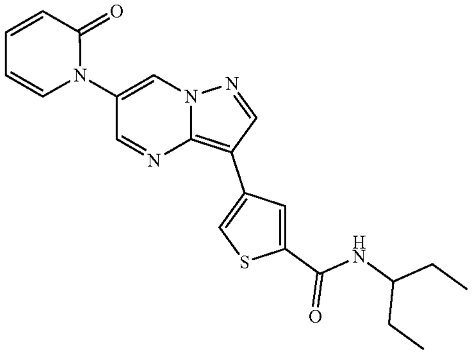 [SMILES: CCC(CC)NC(=O)c1cc(-c2cnn3cc(-n4ccccc4=O)cnc23)cs1] MW 407.49 | $^1$H NMR (500 MHz, Chloroform-d) δ 8.78 (d, J = 2.4 Hz, 1H), 8.58 (d, J = 2.4 Hz, 1H), 8.37 (s, 1H), 8.16 (dd, J = 5.5, 2.0 Hz, 1H), 8.07 (d, J = 1.5 Hz, 1H), 7.99 (d, J = 1.4 Hz, 1H), 7.85-7.77 (m, 1H), 7.16-7.09 (m, 2H), 5.77 (d, J = 9.0 Hz, 1H), 4.02 (dtd, J = 13.4, 8.1, 5.3 Hz, 1H), 1.78-1.48 (m, 4H), 0.95-0.77 (m, 6H). HRMS (ESI) m/z calculated for $C_{21}H_{22}N_5O_2S$ [M + H], 408.1494; found 408.1491. HPLC purity (AUC): 97.6% | 2.93 | — | D | — | — |
| 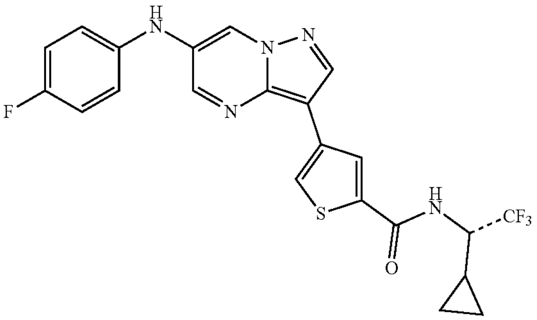 [SMILES: O=C(N[C@@H](C1CC1)C(F)(F)F)c1cc(-c2cnn3cc(Nc4ccc(F)cc4)cnc23)cs1] | 475 | 4.6 | — | A | — | — |

TABLE 1-continued
| Exemplary Compounds | | | | | | |
|---|---|---|---|---|---|---|
| Structure Molecular Weight | NMR and HRMS | cLogP | Kinetic Solubility (μM) | ULK1 $IC_{50}$ | ULK2 $IC_{50}$ | Cell $EC_{50}$ |
| 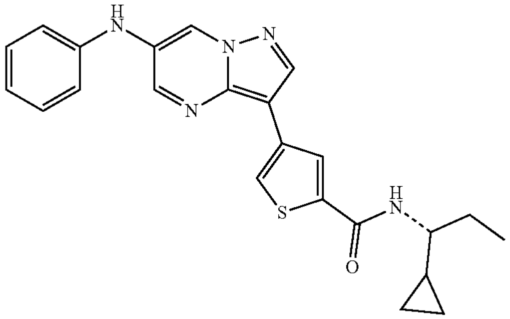 | 418 | 4.3 | — | A | — | — |
| 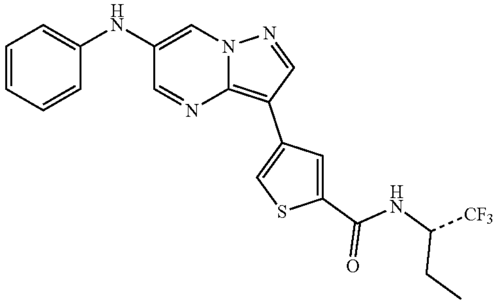 [SMILES: CC[C@H](NC(=O)c1cc(-c2cnn3cc(Nc4ccccc4)cnc23)cs1)C(F)(F)F] | 446 | 4.5 | — | A | — | — |
| 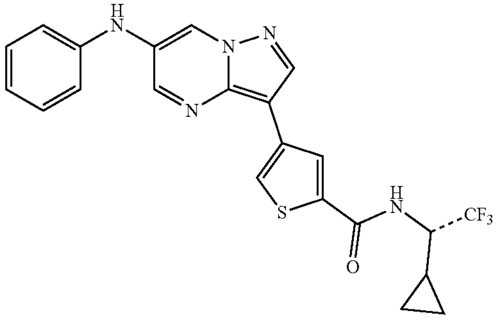 [SMILES: O=C(N[C@@H](C1CC1)C(F)(F)F)c1cc(-c2cnn3cc(Nc4ccccc4)cnc23)cs1] | 458 | 4.5 | — | A | — | — |
| 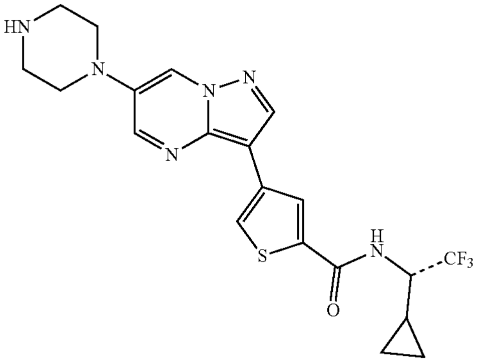 [SMILES: O=C(N[C@@H](C1CC1)C(F)(F)F)c1cc(-c2cnn3cc(N4CCNCC4)cnc23)cs1] | 451 | 2.7 | — | A | — | — |

TABLE 1-continued

| Exemplary Compounds | | | | | | |
|---|---|---|---|---|---|---|
| Structure<br>Molecular Weight | NMR and HRMS | cLogP | Kinetic Solubility (μM) | ULK1 $IC_{50}$ | ULK2 $IC_{50}$ | Cell $EC_{50}$ |
| 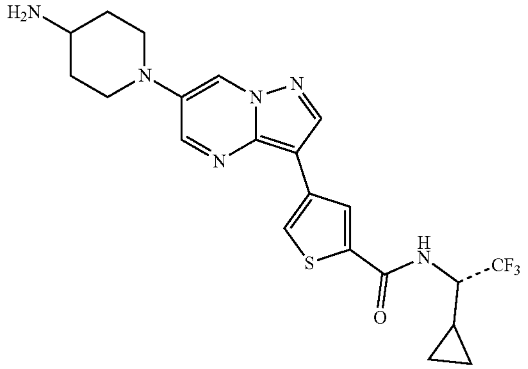 [SMILES: NC1CCN(c2cnc3c(-c4csc(C(=O)N[C@@H](C5CC5)C(F)(F)F)c4)cnn3c2)CC1] | 465 | 2.3 | — | A | — | — |

A = 1-49 nM, B = 50-99 nM, C = 100-499 nM, D = 500-1000 nM, E = >1000 nM

What is claimed:

1. A compound of Formula (I) or (II):

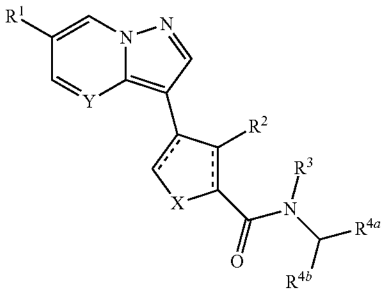

(I)

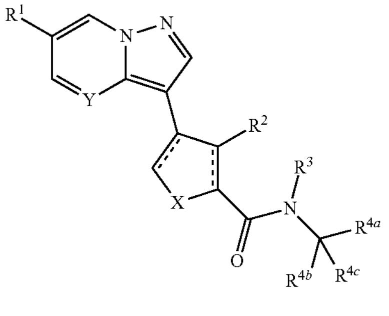

(II)

wherein:

$R^1$ is —N(R$_2$, —N($R^3$)-cycloalkyl, N-attached heterocyclyl, N($R^3$)C(O)OtBu, —N($R^3$)-alkylene-aryl, —N(R-alkylene-heterocyclyl, —N($R^3$)aryl, or —N($R^3$)heterocyclyl;

$R^2$ is H, halo, —CN, —$NO_2$, alkyl, —O-alkyl, —C(O)-alkyl;

$R^3$ is independently H or $C_{1-4}$-alkyl;

$R^{4a}$ and $R^{4b}$ are dependently $C_{1-4}$-alkyl, alkylene-OH, alkylene-N($R^3$)C(O)OtBu, alkylene-N($R^3$)C(O)OtB alkylene-cycloalkyl, cycloalkyl, $CF_3$, or can be taken together to form a 4-7-membered ring;

$R^{4c}$ is H or methyl;

X is O, $NR^3$, or S;

Y is CH or N; and $\overset{-}{---}$ is a single or a double bond;

or a pharmaceutically acceptable salt thereof.

2. The compound of claim 1, wherein the compound of Formula (I) is a compound of Formula (Ia), or (Ib):

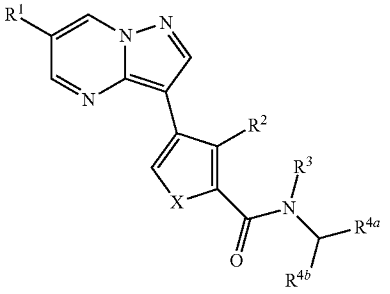

(Ia)

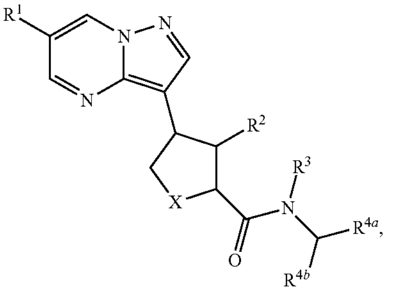

(Ib)

or a pharmaceutically acceptable salt thereof.

3. The compound of claim 1, wherein the compound of Formula (II) is a compound of Formula (IIa), or (IIb):

(IIa)

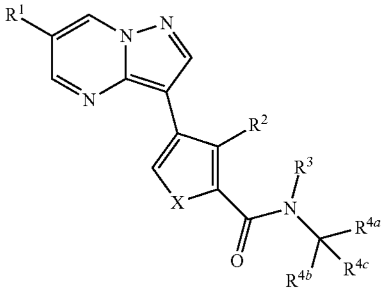

(IIb)

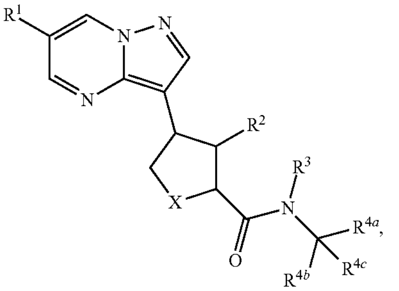

or a pharmaceutically acceptable salt thereof.

4. The compound of claim 1, wherein X is S.

5. The compound of claim 1, wherein $R^1$ is —$N(R^3)_2$—, —$N(R^3)$-cycloalkyl, N-attached heterocyclyl, $N(R^3)$—$C_{5-8}$-aryl, N(H)C(O)OtBu, —$N(R^3)$-alkylene-aryl, or —$N(R^3)$-alkylene-heterocyclyl.

6. The compound of claim 1, wherein $R^1$ is N(H)aryl, —N(H)heterocyclyl.

7. The compound of claim 1, wherein $R^1$ is selected from:

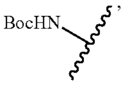,
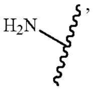,
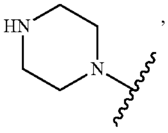,
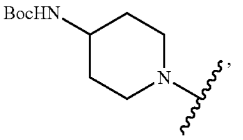,
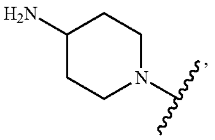,
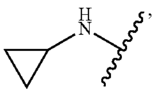,
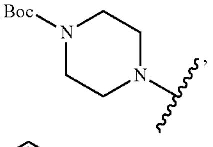,
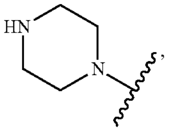,
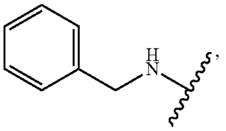,
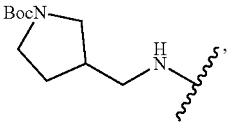,
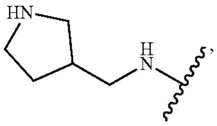, -continued

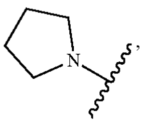,
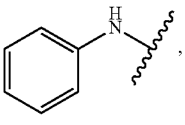,
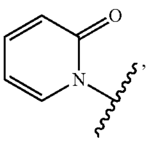,
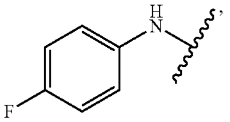,
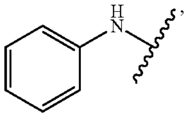, and
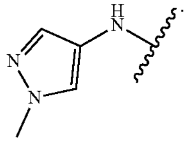.

8. The compound of claim 1, wherein $R^2$ is H.

9. The compound of claim 1, wherein $R^3$ is H.

10. The compound of claim 1, wherein $R^{4a}$ is selected from: —$CH_2OH$, —$CH_2CH_3$, —$CH_2N(H)Boc$ and —$(CH_2)_2N(H)Boc$.

11. The compound of claim 1, wherein $R^{4a}$ and $R^{4b}$ are taken together with the carbon they are attached to form:

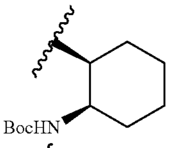,
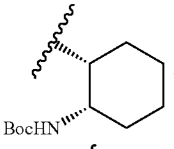,
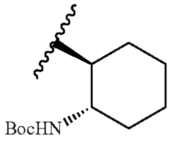, or
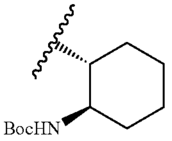.

12. The compound of claim 1, wherein $R^{4a}$ and $R^{4b}$ are taken together with the carbon they are attached to form

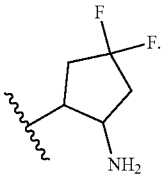 [SMILES: *C1CC(F)(F)CC1N]

13. The compound of claim 1, wherein $R^{4a}$ and $R^{4b}$ are taken together with the carbon they are attached to form

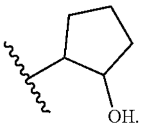 [SMILES: *C1CCCC1O]

14. The compound of claim 1, wherein $R^{4a}$ and $R^{4b}$ are taken together with the carbon they are attached to form
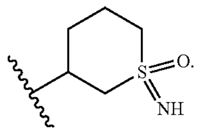 [SMILES: *C1CCCS(=N)(=O)C1]
15. The compound of claim 1, wherein the compound is selected from:
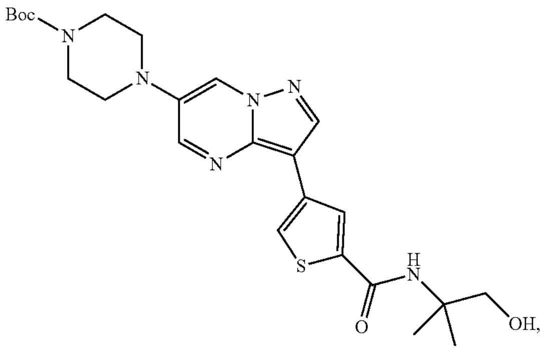
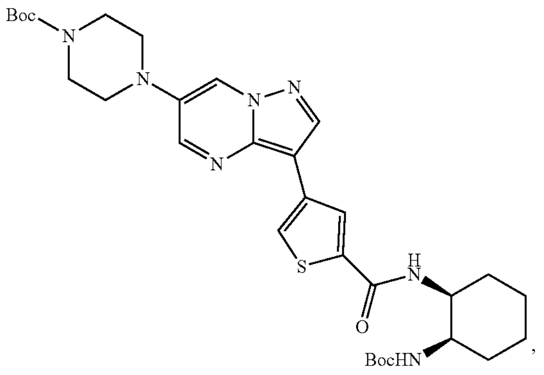
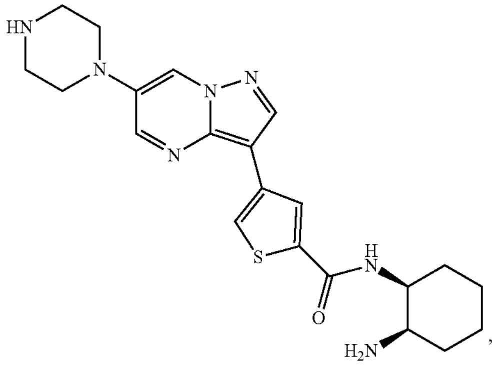
-continued
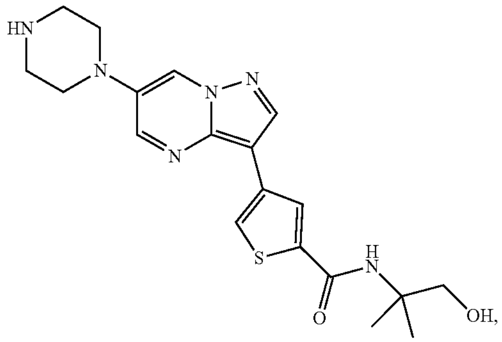
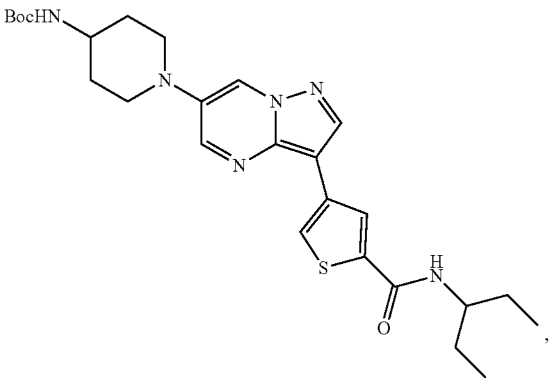
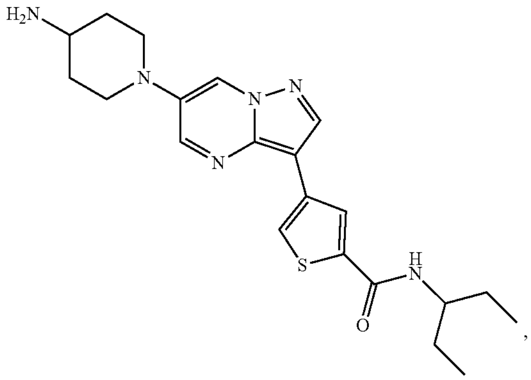
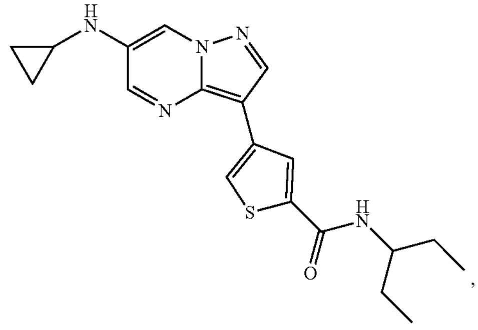

-continued
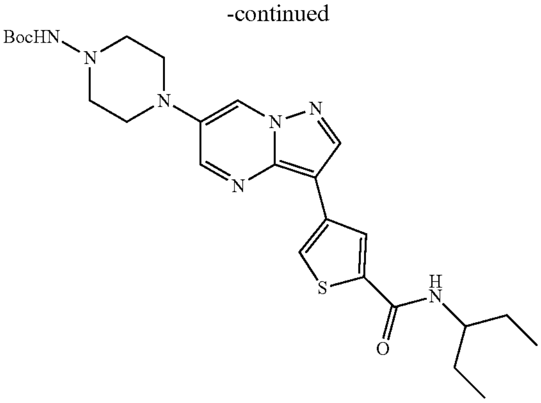
,
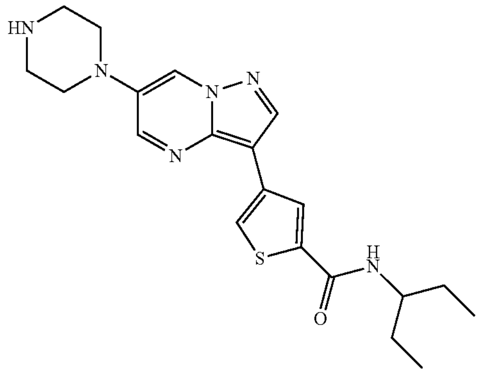
,
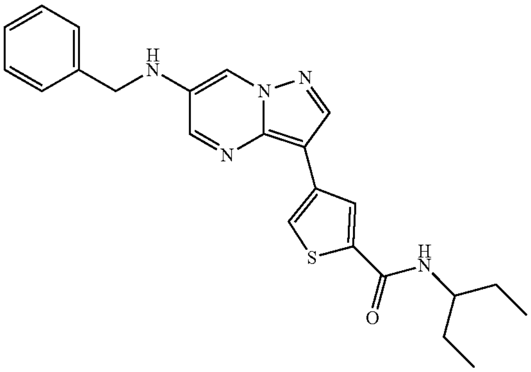
,
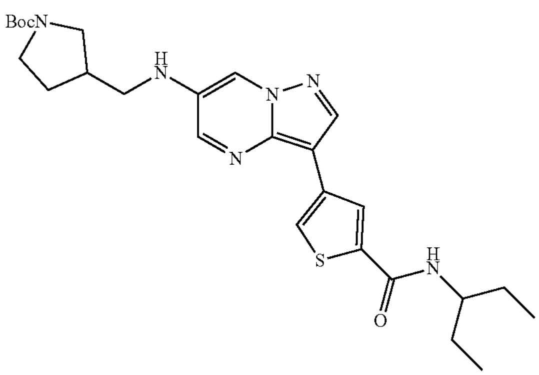
,
-continued
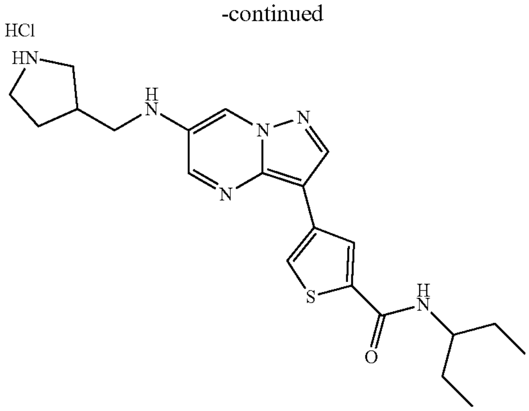
,
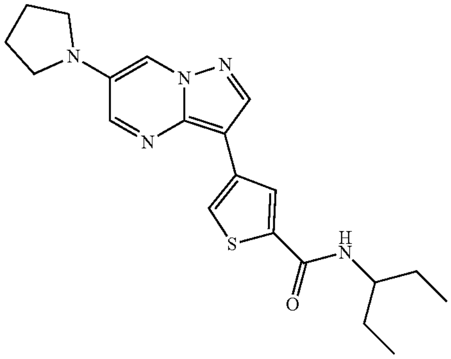
,
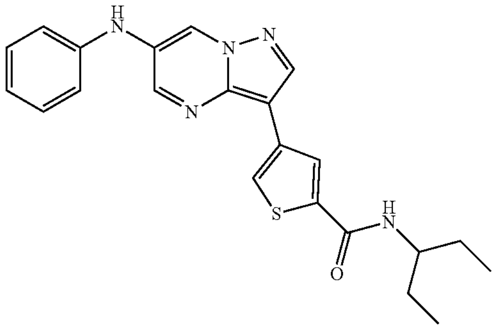
, and
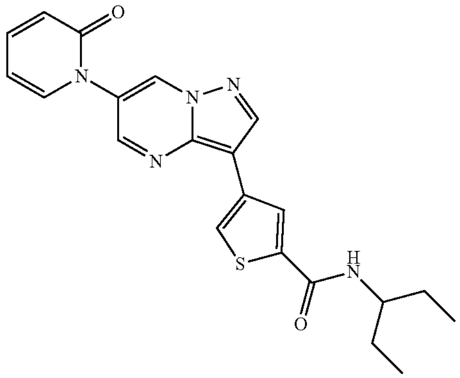
.

16. The compound of claim 1, wherein the compound is selected from:

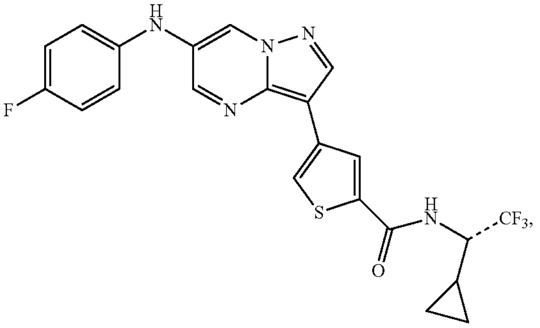

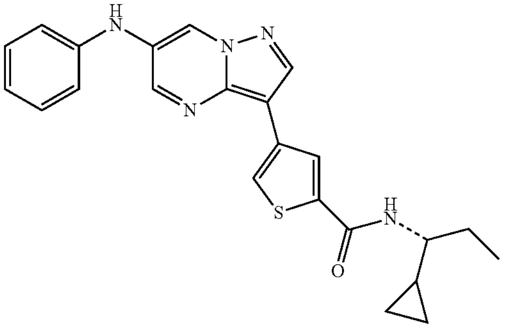

,

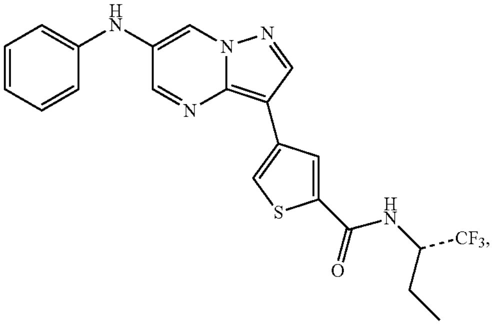

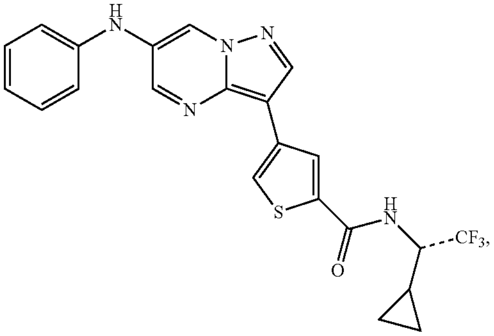

-continued

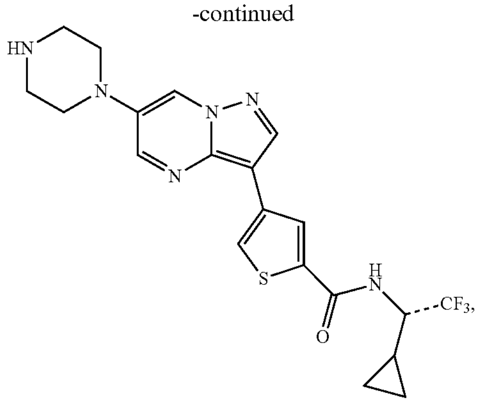

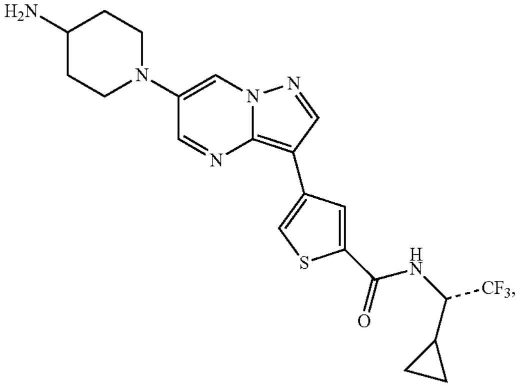

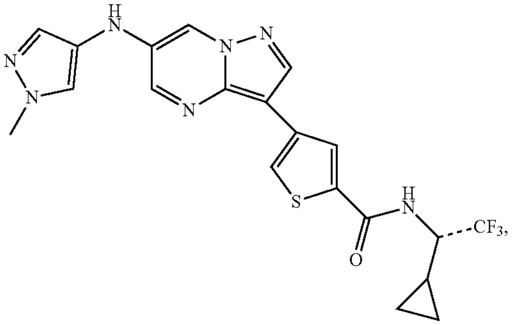

and

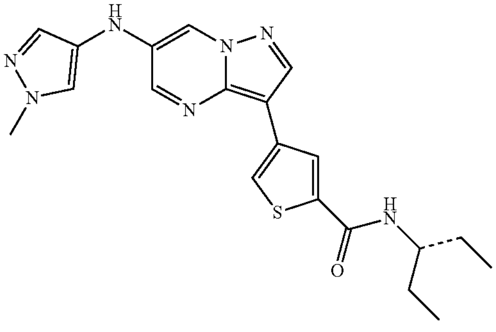

,

17. A pharmaceutical composition comprising a therapeutically effective amount of one or more compounds of claim 1 and at least one pharmaceutical acceptable carrier.

18. A method for treating a cancer or autophagy related diseases, the method comprising administering a therapeutically effective amount of one or more compounds of claim 1 to a patient in need thereof.

19. The method of claim 18, wherein the cancer is lung cancer.

* * * * *